US008309530B2

(12) United States Patent
Szentirmai et al.

(10) Patent No.: US 8,309,530 B2
(45) Date of Patent: Nov. 13, 2012

(54) COMPOSITIONS AND METHODS FOR MODULATING GHRELIN-MEDIATED CONDITIONS

(75) Inventors: Eva Szentirmai, Spokane Valley, WA (US); Levente Kapas, Spokane Valley, WA (US); James M. Krueger, Pullman, WA (US)

(73) Assignee: Washington State University, Pullman, WA (US)

( * ) Notice: Subject to any disclaimer, the term of this patent is extended or adjusted under 35 U.S.C. 154(b) by 0 days.

(21) Appl. No.: 12/700,009

(22) Filed: Feb. 4, 2010

(65) Prior Publication Data

US 2010/0196396 A1 Aug. 5, 2010

Related U.S. Application Data

(60) Provisional application No. 61/149,965, filed on Feb. 4, 2009.

(51) Int. Cl.
*C12N 15/11* (2006.01)
(52) U.S. Cl. .................................................... 514/44 A
(58) Field of Classification Search ................. 514/44 A
See application file for complete search history.

(56) References Cited

U.S. PATENT DOCUMENTS

| 4,816,567 | A | 3/1989 | Cabilly |
| 5,530,101 | A | 6/1996 | Queen |
| 5,585,089 | A | 12/1996 | Queen |
| 5,593,874 | A | 1/1997 | Brown |
| 5,698,425 | A | 12/1997 | Ligon |
| 5,712,135 | A | 1/1998 | D'Halluin |
| 5,789,214 | A | 8/1998 | Ryals |
| 5,804,693 | A | 9/1998 | Gaffney |
| 5,939,598 | A | 8/1999 | Kucherlapati |
| 6,506,559 | B1 | 1/2003 | Fire |
| 6,509,323 | B1 | 1/2003 | Davis |
| 6,884,789 | B2 | 4/2005 | Davis |
| 7,018,609 | B2 | 3/2006 | Hwang Pun |
| 7,091,192 | B1 | 8/2006 | Davis |
| 7,166,302 | B2 | 1/2007 | Hwang Pun |
| 7,270,808 | B2 | 9/2007 | Cheng |
| 2004/0009946 | A1* | 1/2004 | Lewis et al. ............... 514/44 |
| 2006/0229250 | A1* | 10/2006 | Zhang et al. .............. 514/14 |
| 2009/0053169 | A1* | 2/2009 | Castillo et al. ............ 424/85.2 |

FOREIGN PATENT DOCUMENTS

| WO | WO 91/10741 | 7/1991 |
| WO | WO 94/02602 | 2/1994 |
| WO | WO 96/30498 | 10/1996 |
| WO | WO 96/33735 | 10/1996 |
| WO | WO 96/34096 | 10/1996 |
| WO | WO 97/32016 | 9/1997 |
| WO | WO 98/24893 | 6/1998 |
| WO | WO 99/53050 | 10/1999 |
| WO | WO 01/12824 | 2/2001 |
| WO | WO 02/059294 | 8/2002 |
| WO | WO 03/070918 | 8/2003 |
| WO | WO 03/076619 | 9/2003 |
| WO | WO 2005/047505 | 5/2005 |
| WO | WO 2006/044322 | 4/2006 |
| WO | WO 2007/128477 | 11/2007 |

OTHER PUBLICATIONS

Holen et al. (2002) Nucleic Acids Res. 30:1757-1766.*
Harborth et al. (2001) J. Cell Science 114:4557-4565.*
Boese et al., "Mechanical Insights Aid Computational Short Interfering RNA Design," Methods in Enzymology 392:73-96, 2005.*
Reynolds et al., "Rational siRNA design for RNA interference," Nature Biotechnology 22:326-330, 2004).*
Seim et al. BMC Genomics 2007 8:298, pp. 1-16.*
Li et al. (Cell. Mol. Life Sci. 64, 2007, 1785-1792).*
Tiles, 2009, Current Opinion in Molecular Therapeutics 11:156-164.*
U.S. Appl. No. 60/502,050, pp. 1-63, Sep. 10, 2003.*
Alföldi et al., "Brain and core temperatures and peripheral vasomotion during sleep and wakefulness at various ambient temperatures in the rat," Pflügers Archive, 1990, pp. 336-341, vol. 417.
Berger, "Slow Wave Sleep, Shallow Torpor and Hibernation: Homologous States of Diminished Metabolism and Body Temperature," Biological Psychology, 1984, pp. 305-326, vol. 19.
Bodosi et al., "Rhythms of ghrelin, leptin, and sleep in rats: effects of the normal diurnal cycle, restricted feeding, and sleep deprivation," American Journal of Physiology. Regulatory, Integrative, Comparative Physiology, 2004, pp. R1071-R1079, vol. 287.
Bresciani et al., "Obestatin inhibits feeding but does not modulate GH and corticosterone secretion in the rat," Journal of Endocrinological Investigation, 2006, pp. RC16-RC18, vol. 29.
Carlini et al., "Obestatin improves memory performance and causes anxiolytic effects in rats," Biochemical and Biophysiological Research Communications, 2007, pp. 907-912, vol. 352.
Cerri et al., "Cold Exposure and Sleep in the Rat: Effects on Sleep Architecture and the Electroencephalogram," Sleep, 2005, pp. 694-705, vol. 28.
Chothia et al., "Canonical Structures of the Hypervariable Regions of Immunoglobulins," Journal of Molecular Biology, 1987, pp. 901-917, vol. 196.
Cowley et al., "The Distribution and Mechanism of Action of Ghrelin in the CNS Demonstrates a Novel Hypothalamic Circuit Regulating Energy Homeostasis," Neuron, 2003, pp. 649-661, vol. 37.

(Continued)

*Primary Examiner* — Brian Whiteman

(74) *Attorney, Agent, or Firm* — Barry L. Davison; Davis Wright Tremaine LLP

(57) ABSTRACT

In certain aspects, the preproghrelin gene, but not the ghrelin receptor (GHS-R1a) is required for normal integration of thermoregulation and sleep in mice. Particular aspects provide methods for modulation of thermoregulation and other ghrelin-mediated conditions (e.g., reduction of appetite or food intake, reduction of body weight or treatment of obesity, reduction of body temperature or induction of hypothermia, etc.), comprising administration of an inhibitor of ghrelin expression, and including, e.g., siRNA inhibition for treatment of obesity and for modulation of thermoregulation (e.g., induction of hypothermia in surgical settings benefiting from same). Additionally provided are methods for reducing body temperature or induction of hypothermia, comprising administration to a mammalian subject in need thereof an amount of an anti-obestatin antibody agent sufficient to reduce body temperature or induce hypothermia. Further methods comprise administration of a ghrelin peptide antagonist.

12 Claims, 5 Drawing Sheets

OTHER PUBLICATIONS

Cummings, "Ghrelin and the short- and long-term regulation of appetite and body weight," Physiology and Behavior, 2006, pp. 71-84, vol. 89.
Cummings et al., "A Preprandial Rise in Plasma Ghrelin Levels Suggests a Role in Meal Initiation in Humans," Diabetes, 2001, pp. 1714-1719, vol. 50.
Czeisler et al., "Human Sleep: Its Duration and Organization Depend on Its Circadian Phase," Science, 1980, pp. 1264-1267, vol. 210.
De Smet et al., "Effect of peripheral obestatin on gastric emptying and intestinal contractility in rodents," Neurogastroenterology and Motility, 2007, pp. 211-217, vol. 19.
De Smet et al., "Energy Homeostasis and Gastric Emptying in Ghrelin Knockout Mice," The Journal of Pharmacology and Experimental Therapeutics, 2006, pp. 431-439, vol. 316.
Dijk et al., "Contribution of the Circadian Pacemaker and the Sleep Homeostat to Sleep Propensity, Sleep Structure, Electroencephalographic Slow Waves, and Sleep Spindle Activity in Humans," The Journal of Neuroscience, 1995, pp. 3526-3538, vol. 15.
Elbashir et al., "Analysis of gene function in somatic mammalian cells using small interfering RNAs," Methods, 2002, pp. 199-213, vol. 26.
Elbashir et al., "Functional anatomy of siRNAs for mediating efficient RNAi in *Drosophila melanogaster* embryo lysate," The EMBO Journal, 2001, pp. 6877-6888, vol. 20.
Franken et al., "Effects of 12-h Sleep Deprivation and of 12-h Cold Exposure on Sleep Regulation and Cortical Temperature in the Rat," Physiology and Behavior, 1993, pp. 885-894, vol. 54.
Gavrilova et al., "Torpor in mice is induced by both leptin-dependent and -independent mechanisms," The Proceedings of the National Academy of Sciences, 1999, pp. 14623-14628, vol. 96.
Geiser et al., "Leptin increases energy expenditure of a marsupial by inhibition of daily torpor," American Journal of Physiology, 1998, pp. R1627-R1632, vol. 275, 5 Part 2.
Gitlin et al., "Nucleic Acid-Based Immune System: the Antiviral Potential of Mammalian RNA Silencing," Journal of Virology, 2003, pp. 7159-7165, vol. 77.
Glick et al., *Molecular Biotechnology: Principles and Applications of Recombinant DNA*, Editors: Glick et al., 1998, ASM Press, Washington, DC, pp. 160-161.
Gluck et al., "Peripheral ghrelin deepens torpor bouts in mice through the arcuate nucleus neuropeptide Y signaling pathway," American Journal of Physiology. Regulatory, Integrative, Comparative Physiology, 2006, pp. R1303-R1309, vol. 291.
Gourcerol et al., "Lack of interaction between peripheral injection of CCK and obestatin in the regulation of gastric satiety signaling in rodents," Peptides, 2006, pp. 2811-2819, vol. 27.
Hale et al., "Sleep-waking pattern and body temperature in hypoxia at selected ambient temperatures," Journal of Applied Physiology, 1984, pp. 1564-1568, vol. 57.
Himms-Hagen, "Food restriction increases torpor and improves brown adipose tissue thermogenesis in ob/ob mice," American Journal of Physiology, 1985, pp. E531-E539, vol. 248 (5 Part 1).
Hoogenboom et al., "Antibody phage display technology and its applications," Immunotechnology, 1998, pp. 1-20, vol. 4.
Hoogenboom, "Designing and optimizing library selection strategies for generating high-affinity antibodies," Trends in Biotechnology, 1997, pp. 62-70, vol. 15.
Jones et al., "Replacing the complementarity-determining regions in a human antibody with those from a mouse," Nature, 1986, pp. 522-525, vol. 321.
Kettleborough et al., "Humanization of a mouse monoclonal antibody by CDR-grafting: the importance of framework residues on loop conformation," Protein Engineering, 1991, pp. 773-783, vol. 4.
Kojima et al., "Ghrelin is a growth-hormone-releasing acylated peptide from stomach," Nature, 1999, pp. 656-660, vol. 402.
Lagaud et al., "Obestatin reduces food intake and suppresses body weight gain in rodents," Biochemical and Biophysical Research Communications, 2007, pp. 264-269, vol. 357.
Larkin et al., "The Disappearing Slow Wave Activity of Hibernators," Sleep Research Online: SRO, 1998, pp. 96-101, vol. 1.
Lawrence et al., "Acute Central Ghrelin and GH Secretagogues Induce Feeding and Activate Brain Appetite Centers," Endocrinology, 2002, pp. 155-162, vol. 143.
Lu et al., "Immunocytochemical observation of ghrelin-containing neurons in the rat arcuate nucleus," Neuroscience Letters, 2002, pp. 157-160, vol. 321.
Martin, "Ein neuer Zugang zu 2'-O-Alkylribonucleosiden und Eigenschaften deren Oligonucleotide," Separatum Helvetic Chimica Acta, 1995, pp. 486-504, vol. 78.
McCafferty et al., "Phage antibodies: filamentous phage displaying antibody variable domains," Nature, 1990, pp. 552-554, vol. 348.
McGuinness et al., "Phage diabody repertoires for selection of large numbers of bispecific antibody fragments," Nature Biotechnology, 1996, pp. 1149-1154, vol. 14.
Milhavet et al., "RNA Interference in Biology and Medicine," Pharmacological Reviews, 2003, pp. 629-648, vol. 55.
Morrison et al., "Chimeric human antibody molecules: Mouse antigen-binding domains with human constant region domains," The Proceedings of the National Academy of Sciences, 1984, pp. 6851-6855, vol. 81.
Morrison et al., "Genetically Engineered Antibody Molecules," Advances in Immunology, 1989, pp. 65-92, vol. 44.
Muccioli et al., "Ghrelin and des-acyl ghrelin both inhibit isoproterenol-induced lipolysis in rat adipocytes via a non-type 1a growth hormone secretagogue receptor," European Journal of Pharmacology, 2004, pp. 27-35, vol. 498.
Padlan, "Anatomy of the Antibody Molecule," Molecular Immunology, 1994, pp. 169-217, vol. 31.
Padlan, "A Possible Procedure for Reducing the Immunogenicity of Antibody Variable Domains While Preserving Their Ligand-Binding Properties," Molecular Immunology, 1991, pp. 489-498, vol. 28.
Pappenheimer et al., "Extraction of Sleep-Promoting Factor S From Cerebrospinal Fluid and From Brains of Sleep-Deprived Animals," Journal of Neurophysiology, 1975, pp. 1299-1311, vol. 38.
Parmeggiani et al., "Sleep Phases at Low Environmental Temperature," Archivio di Scienze Biologiche, 1969, pp. 277-290, vol. 53.
Reinsch et al., "Amphoteric liposomes as a platform for multi-organ delivery of oligonucleotides," Nanotech, Nanotechnology 2008: Life Sciences, Medicine & Bio Materials—Technical Proceedings of the 2008 NSTI Nanotechnology Conference and Trade Show, Chapter 4: Drug and Gene Delivery Systems, 2008, pp. 328-331, vol. 2.
Roussel et al., "Effect of Ambient Temperataure on the Sleep-Waking Cycle in Two Strains of Mice," Brain Research, 1984, pp. 67-73, vol. 294.
Sakaguchi et al., "Influence of hypothalamic and ambient temperatures on sleep in kangaroo rats," American Journal of Physiology, 1979, pp. R80-R88, vol. 237.
Schmidek et al., "Influence of Environmental Temperature on the Sleep-Wakefulness Cycle in the Rat," Physiology and Behavior, 1972, pp. 363-371, vol. 8.
Schwab et al., "Highly Specific Gene Silencing by Artificial MicroRNAs in *Arabidopsis*," The Plant Cell, 2006, pp. 1121-1133, vol. 18.
Soto et al., "Glucan Particles as an Efficient siRNA Delivery Vehicle," Nanotech, Nanotechnology 2008: Life Sciences, Medicine & Bio Materials—Technical Proceedings of the 2008 NSTI Nanotechnology Conference and Trade Show, Chapter 4: Drug and Gene Delivery Systems, 2008, pp. 332-335, vol. 2.
Strijkstra et al., "Dissimilarity of slow-wave activity enhancement by torpor and sleep deprivation in a hibernator," American Journal of Physiology, 1998, pp. R1110-R1117, vol. 275, No. 4.
Sun et al., "Characterization of Adult Ghrelin and Ghrelin Receptor Knockout Mice under Positive and Negative Energy Balance," Endocrinology, 2008, pp. 843-850, vol. 149.
Sun et al., "Deletion of Ghrelin Impairs neither Growth nor Appetite," Molecular and Cellular Biology, 2003, pp. 7973-7981, vol. 23.
Sun et al., "Ghrelin stimulation of growth hormone release and appetite is mediated through the growth hormone secretagogue receptor," The Proceedings of the National Academy of Sciences, 2004, pp. 4679-4684, vol. 101.
Swoap et al., "AMP does not induce torpor," American Journal of Physiology. Regulatory, Integrative, Comparative Physiology, 2007, pp. R468-R473, vol. 293.

Szentirmai et al., "Ghrelin-induced sleep responses in ad libitum fed and food-restricted rats," Brain Research, 2006, pp. 131-140, vol. 1088.

Szentirmai et al., "Ghrelin microinjection into forebrain sites induces wakefulness and feeding in rats," American Journal of Physiology. Regulatory, Integrative, Comparative Physiology, 2007, pp. R575-R585, vol. 292.

Szentirmai et al., "Obestatin alters sleep in rats," Neuroscience Letters, 2006, pp. 222-226, vol. 404.

Szentirmai et al., "Spontaneous sleep and homeostatic sleep regulation in ghrelin knockout mice," American Journal of Physiology. Regulatory, Integrative, Comparative Physiology, 2007, pp. R510-R517, vol. 293.

Theander-Carrillo et al., "Ghrelin action in the brain controls adipocyte metabolism," The Journal of Clinical Investigation, 2006, pp. 1983-1993, vol. 116.

Toshinai et al., "Des-Acyl Ghrelin Induces Food Intake by a Mechanism Independent of the Growth Hormone Secretagogue Receptor," Endocrinology, 2006, pp. 2306-2314, vol. 147.

Tschöp et al., "Post-prandial decrease of circulating human ghrelin levels," Journal of Endocrinological Investigations, 2001, pp. RC19-RC21, vol. 24.

Verhoeyen et al., "Reshaping Human Antibodies: Grafting an Antilysozyme Activity," Science, 1988, pp. 1534-1536, vol. 239.

Webb et al., "Fasting-Induced Torpor in *Mus musculus* and its Implications in the Use of Murine Models for Human Obesity Studies," Comparative Biochemistry and Physiology. A, Comparative Physiology; 1982, pp. 211-219, vol. 72.

Yasuda et al., "Centrally administered ghrelin suppresses sympathetic nerve activity in brown adipose tissue of rats," Neuroscience Letters, 2003, pp. 75-78, vol. 349.

Zhang et al., "Obestatin, a Peptide Encoded by the Ghrelin Gene, Opposes Ghrelin's Effects on Food Intake," Science, 2005, pp. 996-999, vol. 310.

\* cited by examiner

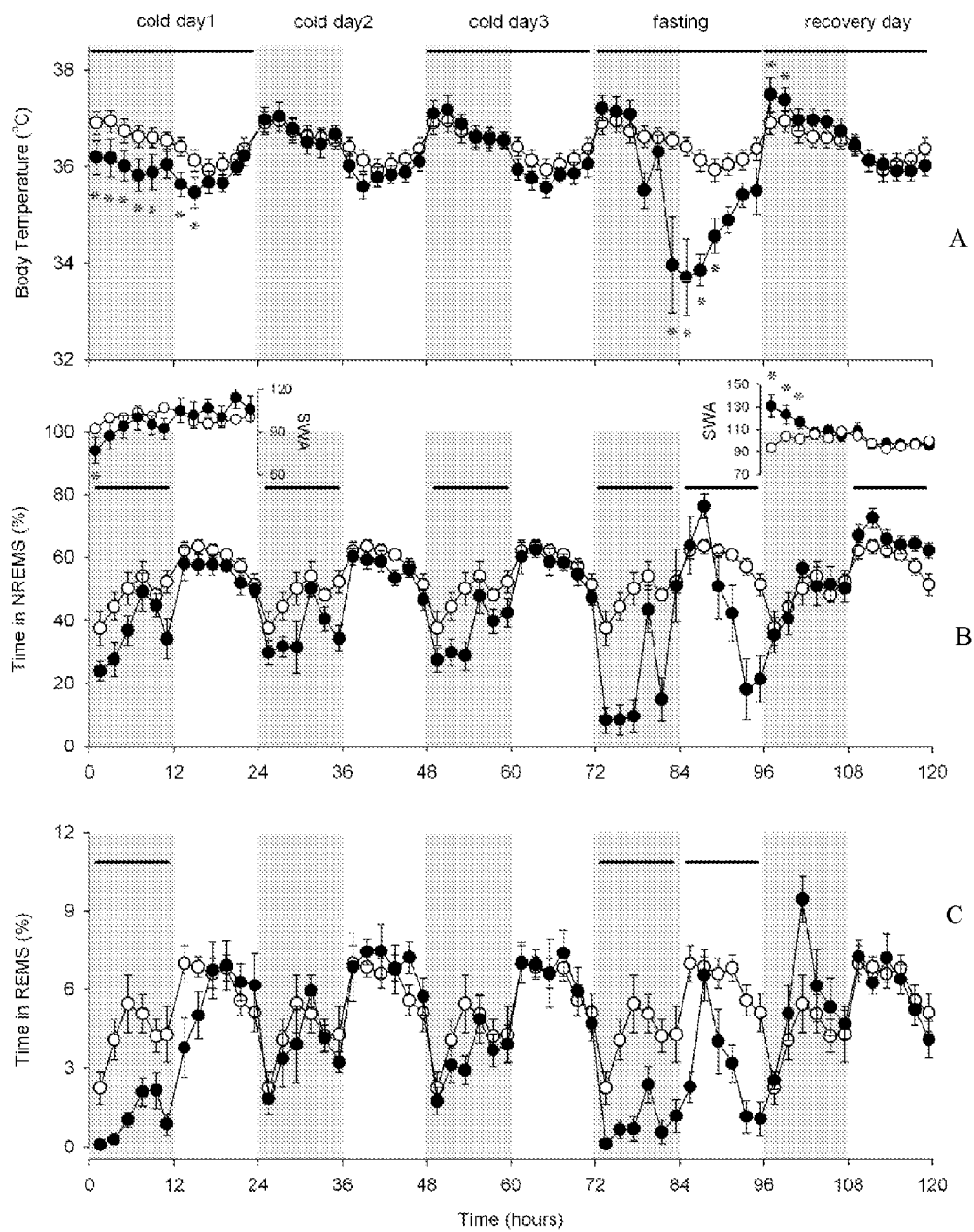
FIGURES 4A-C

SEQUENCE LISTING

```
<160> NUMBER OF SEQ ID NOS: 18

<210> SEQ ID NO 1
<211> LENGTH: 354
<212> TYPE: DNA
<213> ORGANISM: Homo sapiens

<400> SEQUENCE: 1
atgccctccc cagggaccgt ctgcagcctc ctgctcctcg gcatgctctg gctggacttg      60
gccatggcag gctccagctt cctgagccct gaacaccaga gagtccagca gagaaaggag     120
tcgaagaagc caccagccaa gctgcagccc cgagctctag caggctggct ccgcccggaa     180
gatggaggtc aagcagaagg ggcagaggat gaactggaag tccggttcaa cgccccvttt     240
gatgttggaa tcaagctgtc aggggttcag taccagcagc acagccaggc cctggggaag     300
tttcttcagg acatcctctg ggaagaggcc aaagaggccc cagccgacaa gtga          354
```

```
<210> SEQ ID NO 2
<211> LENGTH: 351
<212> TYPE: DNA
<213> ORGANISM: Homo sapiens

<400> SEQUENCE: 2
atgccctccc cagggaccgt ctgcagcctc ctgctcctcg gcatgctctg gctggacttg      60
gccatggcag gctccagctt cctgagccct gaacaccaga gagtccagag aaaggagtcg     120
aagaagccac cagccaagct gcagccccga gctctagcag gctggctccg cccggaagat     180
ggaggtcaag cagaaggggc agaggatgaa ctggaagtcc ggttcaacgc ccccttttgat   240 gttggaatca agctgtcagg ggttcagtac cagcagcaca gccaggccct ggggaagttt     300
cttcaggaca tcctctggga agaggccaaa gaggccccag ccgacaagtg a              351

<210> SEQ ID NO 3
<211> LENGTH: 318
<212> TYPE: DNA
<213> ORGANISM: Homo sapiens

<400> SEQUENCE: 3
atgtttactt gctggtggtc ttatctaaga tcaacattgg cagctgtgcc cggagaggcc      60
tccagggtcc agcagagaaa ggagtcgaag aagccaccag ccaagctgca gccccgagct     120
ctagcaggct ggctccgccc ggaagatgga ggtcaagcag aaggggcaga ggatgaactg     180
gaagtccggt tcaacgcccc ctttgatgtt ggaatcaagc tgtcaggggt tcagtaccag     240
cagcacagcc aggccctggg gaagtttctt caggacatcc tctgggaaga ggccaaagag     300
gccccagccg acaagtga                                                   318

<210> SEQ ID NO 4
<211> LENGTH: 315
<212> TYPE: DNA
<213> ORGANISM: Homo sapiens

<400> SEQUENCE: 4
atgtttactt gctggtggtc ttatctaaga tcaacattgg cagctgtgcc cggagaggcc      60
tccagggtcc agagaaagga gtcgaagaag ccaccagcca agctgcagcc ccgagctcta     120
gcaggctggc tccgcccgga agatggaggt caagcagaag gggcagagga tgaactggaa     180
gtccggttca cgccccctt tgatgttgga atcaagctgt caggggttca gtaccagcag     240
cacagccagg ccctggggaa gtttcttcag gacatcctct gggaagaggc caaagaggcc     300
ccagccgaca agtga                                                      315

<210> SEQ ID NO 5
<211> LENGTH: 201
<212> TYPE: DNA
<213> ORGANISM: Homo sapiens

<400> SEQUENCE: 5
atgtttactt gctggtggtc ttatctaaga tcaacattgg cagctgtgcc cggagaggcc      60
tccagggtcc agttcaacgc ccccttttgat gttggaatca agctgtcagg ggttcagtac    120
cagcagcaca gccaggccct ggggaagttt cttcaggaca tcctctggga agaggccaaa    180
gaggccccag ccgacaagtg a                                               201

<210> SEQ ID NO 6
<211> LENGTH: 276
```

```
<212> TYPE: DNA
<213> ORGANISM: Homo sapiens

<400> SEQUENCE: 6
atgccctccc cagggaccgt ctgcagcctc ctgctcctcg gcatgctctg gctggacttg      60
gccatggcag gctccagctt cctgagccct gaacaccaga gagtccagca gagaaaggag     120
tcgaagaagc caccagccaa gctgcagccc cgagctctag caggctggct ccgcccggaa     180
gatggaggtc aagcagaagg ggcagaggat gaactggaag tccggaggcc ccagccgaca     240
agtgatcgcc acaagccttt actcacctct ctctaa                               276

<210> SEQ ID NO 7
<211> LENGTH: 117
<212> TYPE: PRT
<213> ORGANISM: Homo sapiens

<400> SEQUENCE: 7

Met Pro Ser Pro Gly Thr Val Cys Ser Leu Leu Leu Gly Met Leu
1               5                  10                  15

Trp Leu Asp Leu Ala Met Ala Gly Ser Ser Phe Leu Ser Pro Glu His
            20                  25                  30

Gln Arg Val Gln Gln Arg Lys Glu Ser Lys Lys Pro Ala Lys Leu
        35                  40                  45

Gln Pro Arg Ala Leu Ala Gly Trp Leu Arg Pro Glu Asp Gly Gly Gln
    50                  55                  60

Ala Glu Gly Ala Glu Asp Glu Leu Glu Val Arg Phe Asn Ala Pro Phe
65                  70                  75                  80

Asp Val Gly Ile Lys Leu Ser Gly Val Gln Tyr Gln Gln His Ser Gln
                85                  90                  95

Ala Leu Gly Lys Phe Leu Gln Asp Ile Leu Trp Glu Glu Ala Lys Glu
            100                 105                 110

Ala Pro Ala Asp Lys
        115

<210> SEQ ID NO 8
<211> LENGTH: 116
<212> TYPE: PRT
<213> ORGANISM: Homo sapiens

<400> SEQUENCE: 8

Met Pro Ser Pro Gly Thr Val Cys Ser Leu Leu Leu Gly Met Leu
1               5                  10                  15

Trp Leu Asp Leu Ala Met Ala Gly Ser Ser Phe Leu Ser Pro Glu His
            20                  25                  30

Gln Arg Val Gln Arg Lys Glu Ser Lys Lys Pro Ala Lys Leu Gln
        35                  40                  45

Pro Arg Ala Leu Ala Gly Trp Leu Arg Pro Glu Asp Gly Gly Gln Ala
    50                  55                  60

Glu Gly Ala Glu Asp Glu Leu Glu Val Arg Phe Asn Ala Pro Phe Asp
65                  70                  75                  80

Val Gly Ile Lys Leu Ser Gly Val Gln Tyr Gln Gln His Ser Gln Ala
                85                  90                  95

Leu Gly Lys Phe Leu Gln Asp Ile Leu Trp Glu Glu Ala Lys Glu Ala
            100                 105                 110

Pro Ala Asp Lys
        115
```

```
<210> SEQ ID NO 9
<211> LENGTH: 105
<212> TYPE: PRT
<213> ORGANISM: Homo sapiens

<400> SEQUENCE: 9

Met Phe Thr Cys Trp Trp Ser Tyr Leu Arg Ser Thr Leu Ala Ala Val
1               5                   10                  15

Pro Gly Glu Ala Ser Arg Val Gln Gln Arg Lys Glu Ser Lys Lys Pro
            20                  25                  30

Pro Ala Lys Leu Gln Pro Arg Ala Leu Ala Gly Trp Leu Arg Pro Glu
        35                  40                  45

Asp Gly Gly Gln Ala Glu Gly Ala Glu Asp Glu Leu Glu Val Arg Phe
    50                  55                  60

Asn Ala Pro Phe Asp Val Gly Ile Lys Leu Ser Gly Val Gln Tyr Gln
65                  70                  75                  80

Gln His Ser Gln Ala Leu Gly Lys Phe Leu Gln Asp Ile Leu Trp Glu
                85                  90                  95

Glu Ala Lys Glu Ala Pro Ala Asp Lys
            100                 105

<210> SEQ ID NO 10
<211> LENGTH: 104
<212> TYPE: PRT
<213> ORGANISM: Homo sapiens

<400> SEQUENCE: 10

Met Phe Thr Cys Trp Trp Ser Tyr Leu Arg Ser Thr Leu Ala Ala Val
1               5                   10                  15

Pro Gly Glu Ala Ser Arg Val Gln Arg Lys Glu Ser Lys Lys Pro Pro
            20                  25                  30

Ala Lys Leu Gln Pro Arg Ala Leu Ala Gly Trp Leu Arg Pro Glu Asp
        35                  40                  45

Gly Gly Gln Ala Glu Gly Ala Glu Asp Glu Leu Glu Val Arg Phe Asn
    50                  55                  60

Ala Pro Phe Asp Val Gly Ile Lys Leu Ser Gly Val Gln Tyr Gln Gln
65                  70                  75                  80

His Ser Gln Ala Leu Gly Lys Phe Leu Gln Asp Ile Leu Trp Glu Glu
                85                  90                  95

Ala Lys Glu Ala Pro Ala Asp Lys
            100

<210> SEQ ID NO 11
<211> LENGTH: 66
<212> TYPE: PRT
<213> ORGANISM: Homo sapiens

<400> SEQUENCE: 11

Met Phe Thr Cys Trp Trp Ser Tyr Leu Arg Ser Thr Leu Ala Ala Val
1               5                   10                  15

Pro Gly Glu Ala Ser Arg Val Gln Phe Asn Ala Pro Phe Asp Val Gly
            20                  25                  30

Ile Lys Leu Ser Gly Val Gln Tyr Gln Gln His Ser Gln Ala Leu Gly
        35                  40                  45

Lys Phe Leu Gln Asp Ile Leu Trp Glu Glu Ala Lys Glu Ala Pro Ala
    50                  55                  60

Asp Lys
65
```

<210> SEQ ID NO 12
<211> LENGTH: 91
<212> TYPE: PRT
<213> ORGANISM: Homo sapiens

<400> SEQUENCE: 12

Met Pro Ser Pro Gly Thr Val Cys Ser Leu Leu Leu Gly Met Leu
1               5                   10                  15

Trp Leu Asp Leu Ala Met Ala Gly Ser Ser Phe Leu Ser Pro Glu His
                20                  25                  30

Gln Arg Val Gln Gln Arg Lys Glu Ser Lys Lys Pro Pro Ala Lys Leu
            35                  40                  45

Gln Pro Arg Ala Leu Ala Gly Trp Leu Arg Pro Glu Asp Gly Gly Gln
        50                  55                  60

Ala Glu Gly Ala Glu Asp Glu Leu Glu Val Arg Arg Pro Gln Pro Thr
65                  70                  75                  80

Ser Asp Arg Pro Gln Ala Leu Leu Thr Ser Leu
                85                  90

<210> SEQ ID NO 13
<211> LENGTH: 21
<212> TYPE: DNA
<213> ORGANISM: Artificial Sequence
<220> FEATURE:
<223> OTHER INFORMATION: ghrelin siRNA sequence 1 rat

<400> SEQUENCE: 13
agcugucagg agcucaguat t                                         21

<210> SEQ ID NO 14
<211> LENGTH: 21
<212> TYPE: DNA
<213> ORGANISM: Artificial Sequence
<220> FEATURE:
<223> OTHER INFORMATION: ghrelin siRNA sequence 2 rat

<400> SEQUENCE: 14
ggaaaguuuc uucaggauat t                                         21

<210> SEQ ID NO 15
<211> LENGTH: 21
<212> TYPE: DNA
<213> ORGANISM: Artificial Sequence
<220> FEATURE:
<223> OTHER INFORMATION: ghrelin siRNA sequence 3

<400> SEQUENCE: 15
ggagcuggaa aucagguuct t                                         21

<210> SEQ ID NO 16
<211> LENGTH: 21
<212> TYPE: DNA
<213> ORGANISM: Artificial Sequence
<220> FEATURE:
<223> OTHER INFORMATION: ghrelin siRNA sequence 4 mouse

<400> SEQUENCE: 16
aggcgccagc ugacaaguat t                                         21

<210> SEQ ID NO 17
<211> LENGTH: 21
<212> TYPE: DNA
<213> ORGANISM: Artificial Sequence
<220> FEATURE:

```
<223> OTHER INFORMATION: ghrelin siRNA sequence 5 mouse

<400> SEQUENCE: 17
gguucaaugc ucccuucgat t                                              21

<210> SEQ ID NO 18
<211> LENGTH: 5
<212> TYPE: PRT
<213> ORGANISM: Homo sapiens

<400> SEQUENCE: 18

Phe Asn Ala Pro Phe
1               5
```

COMPOSITIONS AND METHODS FOR MODULATING GHRELIN-MEDIATED CONDITIONS

CROSS-REFERENCE TO RELATED APPLICATIONS

The application claims the benefit of priority to U.S. Provisional Patent Application Ser. No. 61/149,965, filed 4 Feb. 2009 and entitled COMPOSITIONS AND METHODS FOR MODULATING GHRELIN-MEDIATED CONDITIONS, which is incorporated by reference herein in its entirety.

STATEMENT REGARDING FEDERALLY-SPONSORED RESEARCH

This invention was made with government support under grant numbers NS27250, RO1AG18895 and RO1AG1923 awarded by the National Institutes of Health. The United States Government has certain rights in the invention.

FIELD OF THE INVENTION

Aspects of the present invention relate generally to ghrelin-mediated conditions, including but not limited to thermoregulation, obesity and sleep, and in more particular aspects to compositions and methods for modulation of thermoregulation, obesity and sleep in mammals, and for modulation of the ability to manifest and integrate normal sleep and thermoregulatory responses to metabolic challenges in mammals. Particular preferred aspects relate to compositions and methods for treating obesity, and for modulating thermoregulation, comprising administration of anti-ghrelin (e.g., anti-preproghrelin) agents (e.g., small-interfering RNA ("siRNA")) to a mammal in need thereof.

SEQUENCE LISTING

A Sequence Listing comprising SEQ ID NOS:1-18 is incorporated by reference herein in its entirety as part of this application.

BACKGROUND

Preproghrelin is cleaved into at least two distinct peptides, ghrelin (1) and obestatin (2). The major source of circulating ghrelin is the stomach (1) and ghrelin plasma levels inversely correlate with feeding (3, 4). Ghrelin mRNA and ghrelin-like immunoreactivity are also found in the brain (1, 5-8), mainly in the arcuate nucleus and in the internuclear space in the hypothalamus. Ghrelin is involved in the short- and long-term regulation of energy balance by stimulating feeding and suppressing energy expenditure (reviewed in (9)). The role of obestatin in the regulation of feeding and metabolism is less clear. Several (2, 10-12) but not all (13, 14) studies showed that acute administration of obestatin suppresses food intake in rats and mice and repeated obestatin injections lead to suppressed body weight gain in mice suggesting enhanced energy expenditure (10).

Ghrelin and obestatin may also play a role in sleep regulation. Sleep deprivation induces increases in hypothalamic and plasma ghrelin levels (6), and central or systemic administration of ghrelin has a strong wake-promoting effect in rats while the injection of obestatin facilitates sleep in rats (15-17). It is posited that increased wakefulness and feeding are two parallel outputs of a hypothalamic ghrelinergic circuitry that also involve the function of neuropeptide Y-ergic and orexinergic neurons (17). Sleep-wake activity (18) and metabolism (19) of ghrelin knockout (KO) mice are, however, relatively normal if the animals are kept under thermoneutral ambient temperature with food provided ad libitum. Since there are multiple substances involved in the regulation of metabolism and sleep-wake activity, it seems likely that under normal physiological conditions, redundant regulatory systems compensate for the lack of the preproghrelin gene product(s).

SUMMARY OF ASPECTS OF THE INVENTION

As disclosed herein for the first time, the preproghrelin gene, but not the ghrelin receptor (GHS-R1a) is required for normal integration of thermoregulation and sleep in mice. Based on this discovery, particular aspects of the present invention relate to methods for modulation of thermoregulation and other ghrelin-mediated conditions (e.g., reduction of appetite or food intake, reduction of body weight or treatment of obesity, reduction of body temperature or induction of hypothermia, etc.), comprising administration of an inhibitor of ghrelin expression, and including, for example, siRNA inhibition of the peptide products encoded by the preproghrelin gene for treatment of obesity and for modulation of thermoregulation (e.g., induction of hypothermia in surgical settings benefiting from same).

Peptidergic mechanisms controlling feeding, metabolism, thermoregulation and sleep overlap in the hypothalamus. Low ambient temperatures and food restriction induce hypothermic bouts and characteristic metabolic and sleep changes in mice.

According to particular aspects of the present invention, mice lacking the ghrelin gene, but not those lacking the ghrelin receptor, have impaired abilities to manifest and integrate normal sleep and thermoregulatory responses to metabolic challenges. In response to fasting in a cold environment, ghrelin knockout mice first enter mild hypothermic bouts, associated with markedly reduced sleep followed by a precipitous drop in body temperature to near ambient levels. Prior treatment with obestatin, another preproghrelin gene product, attenuates the hypothermic response of ghrelin knockout mice. The results indicate that obestatin is a component in the coordinated regulation of metabolism and sleep.

According to particular aspects, the disclosed ghrelin antagonists have utility in facilitating weight loss, appetite decrease. and weight maintenance, and can be used to treat obesity, diabetes, complications of diabetes (e.g., retinopathy), and/or to treat cardiovascular disorders. Excessive weight is a contributing factor to various diseases including hypertension, diabetes, dyslipidemias, cardiovascular disease, gall stones, osteoarthritis and certain forms of cancers. Facilitating weight loss, for example, can be used to reduce the likelihood of such diseases and as part of a treatment for such diseases.

Particular preferred aspects provide a method for suppressing food intake or appetite, comprising administration to a mammalian subject in need thereof an amount of ghrelin or preproghrelin siRNA sufficient to suppress ghrelin or preproghrelin mRNA, wherein suppression of food intake or appetite is afforded.

Additional aspects provide a method for reducing body weight or treating obesity, comprising administration to a mammalian subject in need thereof an amount of ghrelin or preproghrelin siRNA sufficient to suppress ghrelin or preproghrelin mRNA, wherein reduction of body weight or treating obesity is afforded.

In particular aspects of the above methods, the ghrelin or preproghrelin siRNA, comprises a sequence complementary to a target sequence selected from SEQ ID NOS:1-6, complements thereof, and contiguous portions thereof. In certain aspects, the siRNA comprises a sequence of about 10 to about 100 nucleotides, about 12 to about 25 nucleotides, about 14 to about 22 nucleotides or about 15, 16, 17, 18, 19, 20 or 21 nucleotides complementary to the target sequence. In certain aspects, administration comprises oral delivery. In certain embodiments, the suppression of ghrelin or preproghrelin mRNA is transient or reversible.

Additional aspects provide a method for reducing body temperature or induction of hypothermia, comprising administration to a mammalian subject in need thereof an amount of obestatin siRNA sufficient to suppress obestatin mRNA, wherein reducing body temperature or induction of hypothermia is afforded. In certain aspects, the obestatin siRNA, comprises a sequence complementary to a target sequence selected from SEQ ID NOS:1-6, complements thereof, and contiguous portions thereof. In particular embodiments, the siRNA comprises a sequence of about 10 to about 100 nucleotides, about 12 to about 25 nucleotides, about 14 to about 22 nucleotides or about 15, 16, 17, 18, 19, 20 or 21 nucleotides complementary to the target sequence. In certain embodiments, administration comprises oral delivery. In particular aspects, suppression of obestatin mRNA is transient or reversible. In preferred aspects, reducing body temperature or induction of hypothermia comprises regulating at least one of surgical hypothermia, trauma-related hypothermia, and cardiac-related hypothermia.

Further aspects provide a method for reducing body temperature or induction of hypothermia, comprising administration to a mammalian subject in need thereof an amount of an anti-obestatin antibody agent sufficient to reduce body temperature or induce hypothermia. In particular embodiments, administration of the anti-obestatin antibody agent is concomitant with, or subsequent to, food deprivation.

Yet further aspects provide a method for suppressing food intake or appetite, comprising administration to a mammalian subject in need thereof an amount of a ghrelin peptide antagonist, sufficient to afford suppression of food intake or appetite.

Additional aspects provide a method for reducing body weight or treating obesity, comprising administration to a mammalian subject in need thereof an amount of a ghrelin peptide antagonist, sufficient to afford reduction of body weight or treatment of obesity.

Yet further aspects provide a method for reducing body temperature or induction of hypothermia, comprising administration to a mammalian subject in need thereof an amount of a ghrelin peptide antagonist, sufficient to afford reduction of body temperature or induction of hypothermia.

In certain aspects of the above methods, the ghrelin peptide antagonist comprises a subportion of the full-length ghrelin protein.

BRIEF DESCRIPTION OF THE DRAWINGS

FIG. 4 shows, according to particular exemplary aspects, body temperature, NREMS, SWA and REMS of ghrelin WT mice during the course of the experiment. Experimental manipulations induced significant changes in body temperature and sleep of ghrelin WT mice. The direction of these changes was similar to those seen in KOs. Data statistics and details were as described in relation to the data of FIGS. 1 and 3.

DETAILED DESCRIPTION OF THE INVENTION

Figures 1A, 1B:
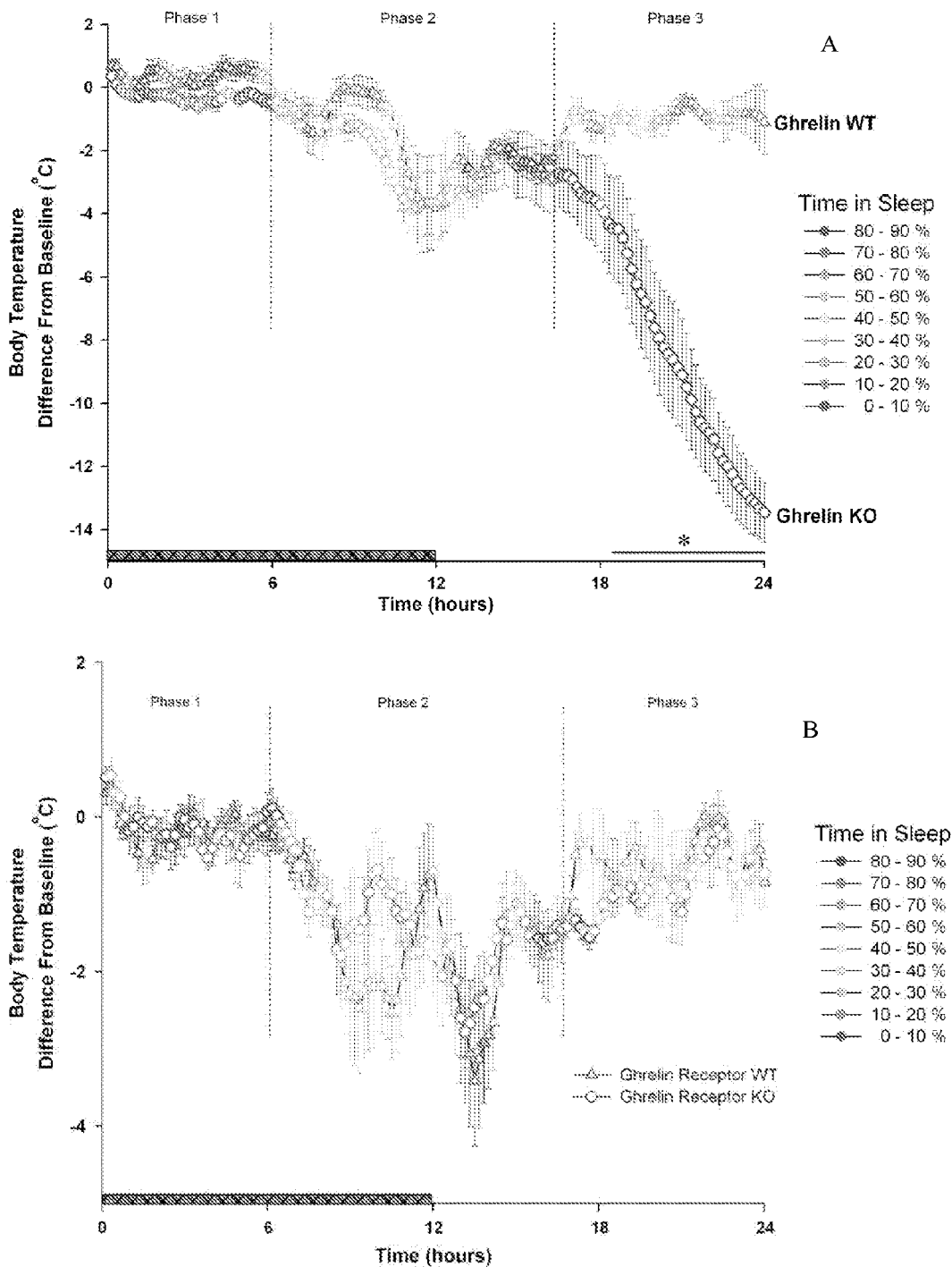
FIGS. 1A and 1B shows the body temperature and the amount of total sleep time in ghrelin wild-type (WT) and knockout (KO) mice (FIG. 1A), and in ghrelin receptor WT and KO mice (FIG. 1B) during the day of fasting. Body temperature data are expressed as difference from baseline in 10-min averages. Body temperature was significantly different between ghrelin WT and ghrelin KO mice [ANOVA, genotype effect $F(1,13)=5.41$, $p<0.05$). Changes in body temperature were not significantly different between ghrelin receptor KO and WT mice (ANOVA, genotype effect $F(1,13)=2.4$, $p>0.05$). The horizontal black bar with asterisk marks the period of significant difference between WT and KO mice (univariate tests of significance for planned comparison, $p<0.05$). The colors of symbols represent the amount of total sleep (expressed as % of recording time) during the 10-min periods. The horizontal grey bar at the bottom of the figures indicates the dark phase of the day period.
Figures 2A, 2B, 2C, 2D:
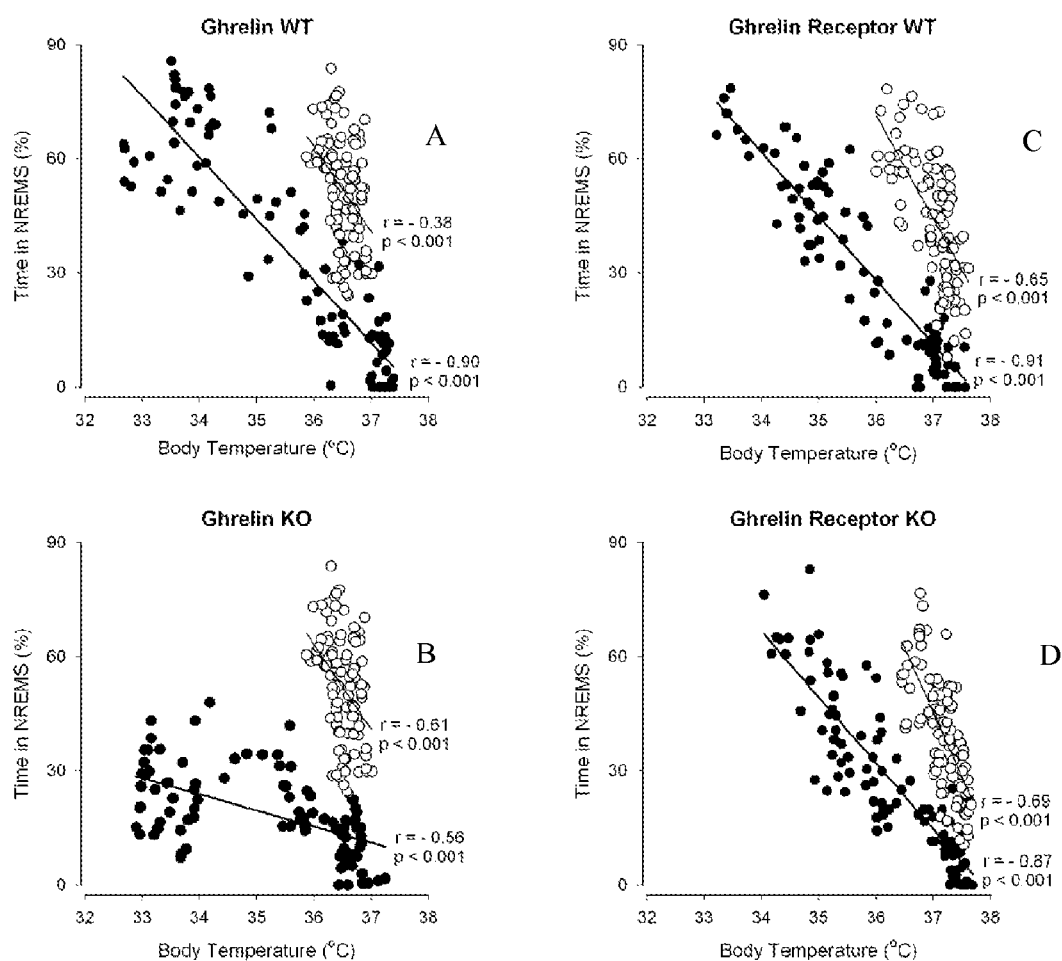
FIGS. 2A-2D show, according to particular exemplary aspects, the correlation between the amount of non-rapid-eye movement sleep (NREMS) and body temperature during hours 1 to 16 on the baseline (open circles) and fasting days (closed circles) in ghrelin WT (FIG. 2A; left, top panel), ghrelin KO (FIG. 2B; left, bottom panel), ghrelin receptor WT (FIG. 2C; right, top panel) and ghrelin receptor KO (FIG. 2D; right, bottom panel) mice. Individual data points represent 10-min temperature (° C.) and NREMS (% of recording time) averages. The relatively weak correlation between body temperature and NREMS duration on the baseline day can be explained by the fact that, in addition to NREMS-related decreases in body temperature (35), there are also sleep-independent, circadian changes in temperature. In response to fasting in a cold environment, the correlation became significantly stronger and the regression line is shifted to the left in ghrelin WT, ghrelin receptor WT and KO mice. This reflects the fact that the hypothermic periods were associated with increases in NREMS but when body temperature was in the 36-37° C. range the dominant state was wakefulness. In ghrelin KO mice (FIG. 2B; left, bottom panel), the slope of regression line became significantly more horizontal on the fasting day [$F(1,188)=112.2$, $p<0.001$], indicating that the integrative mechanisms linking NREMS duration to body temperature are dependent upon the preproghrelin gene. Multiple regression analyses revealed that the correlation between NREMS time and body temperature on the fasting day in ghrelin KO mice is significantly different from ghrelin WT [$F(2,188)=148.3$, $p<0.001$], ghrelin receptor WT [$F(2,188)=166.2$, $p<0.001$] and ghrelin receptor KO mice [$F(2,188)=140.5$, $p<0.001$].

According to particular aspects, and as described in working Examples 1-3 herein below, ghrelin KO mice have greatly increased sensitivity to a combined challenge by low environmental temperature and fasting as measured by their thermoregulatory and sleep responses. In response to food restriction in cold, normal mice generate periodic hypothermic bouts during which they maintain consolidated NREMS episodes and their body temperature gradually returns to normal within 24 h after the removal of food. In ghrelin KO animals, after the periods of hypothermia, body temperature drops precipitously to near-ambient levels and EEG-identifiable sleep-wake cycles disappear. In contrast, ghrelin receptor KO mice did not have impairment in their sleep and temperature responses. This is the first demonstration of a marked phenotypic difference in ghrelin KO and ghrelin receptor KO mice.

According to additional aspects, the deficits observed in ghrelin KO mice are due to the lack of one or more of the products of preproghrelin. The fact that ghrelin receptor KO mice, which produce normal levels of ghrelin, did not show impaired responses indicates that it is unlikely that deficits are due to the lack of ghrelin/GHS-R1a signaling. There may be a second ghrelin receptor subtype in addition to the GHS-R1a receptor (21); if correct, then ghrelin may have acted on such receptors in the GHS-R1a KO animals. Also des-acyl ghrelin, a ghrelin isoform that lacks the n-octanoyl moiety, has ghrelin-like effects on feeding which are independent of the activation of the known ghrelin receptor (22), and it is thus possible that des-acyl ghrelin may be a mediator of maintained thermoregulation and sleep in ghrelin receptor KO mice. Regardless, based on the known effects of ghrelin, the observed deficiencies in ghrelin KO mice are difficult to explain by ghrelin deficiency. Ghrelin induces a positive energy balance by stimulating feeding and decreasing energy expenditure which leads to increased lipogenesis (23). Ghrelin suppresses metabolic heat production in rats (24), causes hypothermia under normal conditions (25) and also deepens hypothermic bouts caused by starvation at low ambient temperature in mice (26).

Additionally, while the herein disclosed deficiencies observed in ghrelin KO animals could possibly be explained by the lack of a leptin-like hormone that promotes the mobilization of energy stores and enhances energy expenditure and metabolic heat production (the lack of leptin facilitates spontaneous as well as food restriction-induced hypothermic bouts (27, 28) while exogenous leptin prevents hypothermia in leptin-deficient mice (29) and attenuates fasting-induced hypothermia in a marsupial (30)), plasma leptin levels in ghrelin KO mice are, however, normal (8).

Likewise, in addition to ghrelin, another product of the ghrelin gene is obestatin. The effects of obestatin on food intake and metabolism appear to be the opposite of those of ghrelin although the results are still inconclusive (2, 10-14). If obestatin has a leptin-like role in the regulation of metabolism, then decreased resistance to metabolic challenge in ghrelin KO mice could be explained by the lack of this hormone. Based on this idea, Applicants attempted to rescue the herein disclosed impaired phenotype by replacing obestatin in ghrelin KO mice. There are several potential ways to do this, although each has its own limitations. The effects of a single bolus injection of obestatin are limited by the half-life of the peptide ($22\pm2$ min). Applicants initially tried to replace obestatin by using multiple injections and found that the injection procedure (with saline) itself interferes with the normally occurring hypothermic response. Nevertheless, preliminary data with bolus injections (not shown) suggested that obestatin attenuated hypothermia in ghrelin KO mice. Because of those limitations, obestatin was replaced using osmotic minipumps. This method also has limitations. The minipumps are filled and implanted at least 10 days before the challenge to allow enough time for recovery and to carry out the experiment. The stability of obestatin in solution at body temperature for such extended time period is unknown. Moreover, some of the biological effects of obestatin show a bell-shaped dose-response relationship. It is unknown whether the amount of obestatin released from the minipumps provides the optimal plasma levels or appropriate pulsatile or ultradian secretion patterns. Nevertheless, obestatin replacement using minipumps significantly delayed the hypothermic response although it did not completely prevent it (See Example 3 herein). This indicates that the lack of obestatin in ghrelin KO mice may, at least in part, be responsible for the observed thermoregulatory deficit.

In addition to ghrelin and obestatin, new mRNA transcripts of the ghrelin gene were described (31) recently. The peptide products of these transcripts have not yet been identified but it is possible that the lack of one of these unidentified products may also contribute to the severe deficits observed in ghrelin KO animals.

There is a clear impairment in maintaining the balance between heat production and energy saving in ghrelin KO animals. While average body temperature is not different from that of WT animals during the second phase of the fasting day, ghrelin KO mice have severely suppressed sleep at this time. It is unlikely that this is due to impairment of the sleep-promoting mechanisms since sleep-wake activity of ghrelin KO mice is not different from WTs under normal conditions (present data and (18)) and ghrelin KO mice are capable of mounting normal rebound sleep increases after sleep deprivation. It is possible, however, that metabolic challenges unveil a subtle impairment in sleep regulation which is not apparent under normal metabolic conditions.

According to particular aspects of the present invention, the primary deficit in ghrelin KO animals is a metabolic deficiency, and enhanced wakefulness serves to supplement failing heat production. This impairment in heat production cannot be explained by a decreased size of energy stores since the body weight of Applicants' ghrelin KO mice was virtually the same as that of WTs and their body composition and adiposity are not different from controls (8). It is more likely that ghrelin KO animals, which rely on fat utilization to a greater extent than normal mice even under normal conditions (8, 32), are impaired in their ability to mobilize extra amount of energy in severe negative metabolic states.

Irrespective of the exact cause, increased wakefulness during the second response phase on the fasting day is likely to lead to the more rapid depletion of the energy stores in ghrelin KO mice, which energy levels then, in phase 3, fall in a positive feedback cycle. Likely, they cannot enter normal sleep because of the danger of collapse of the impaired thermoregulation, such that they maintain prolonged wakefulness leading to further depletion of the energy stores. Mice are able to undergo periods of hypothermia at low ambient temperature when food availability is reduced. This phenomenon, often called torpor, is thought to be analogous to hibernation (33). It is an energy conserving state characterized by the suppression of metabolic rate, heart rate, ventilation and body temperature and metabolism shifts from carbohydrate oxidation to lipid metabolism. All four mouse genotypes displayed hypothermic bouts after food had been removed. These hypothermic bouts appeared to be smaller than those previously reported likely because female, lower weight (22-24 g) mice with a different genetic background were used in prior studies (26, 34).

An association between sleep and temperature-regulation has long been recognized (reviewed in (35)). For example, NREMS is associated with a regulated decrease in body temperature and metabolism and duration of REMS is ambient temperature-dependent. In humans, living under free-running conditions, the duration of sleep episodes correlates with body temperature at bedtime (36, 37). Total sleep time is highest and sleep latency shortest if sleep onset occurs at the body temperature minimum. In addition to the circadian component of body temperature changes, a clear sleep-dependent drop in body temperature is also present in humans (37). Similarly, as described herein, Applicants found strong correlation between body temperature and NREMS time on the fasting day in ghrelin WT, ghrelin receptor WT and KO mice which was absent in ghrelin KO mice (FIG. 2A-2D).

Figures 3A, 3B, 3C:
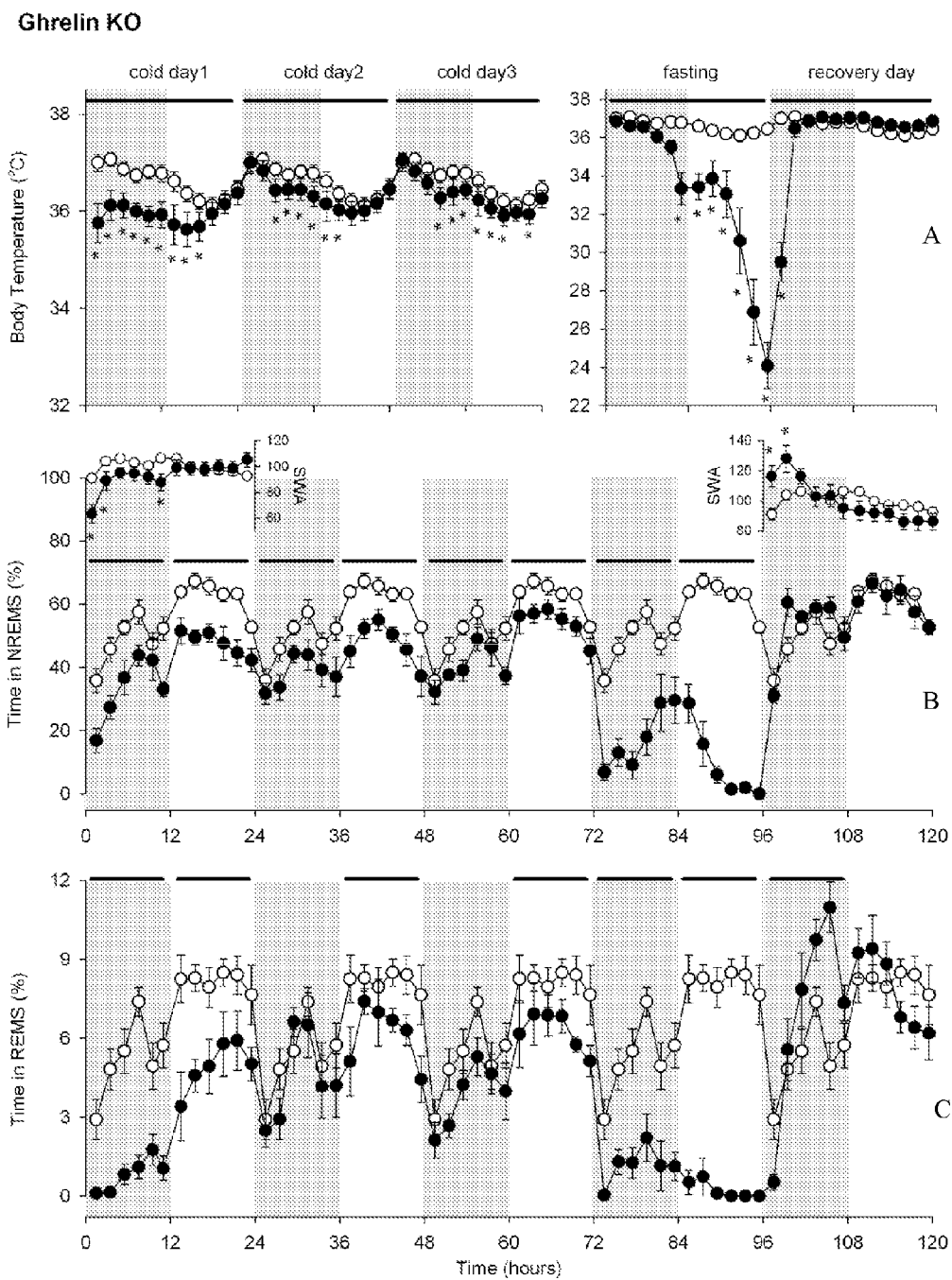
FIGS. 3A-3C show, according to particular exemplary aspects, body temperature (FIG. 3A; top panel), NREMS (FIG. 3B; middle panel), slow wave activity (FIG. 3B; SWA inserts), and rapid-eye-movement sleep (REMS) (FIG. 3C; bottom panel) of ghrelin KO mice during the course of the experiments of Examples 1 and 2 herein. On the baseline day, body temperature, NREMS, REMS and EEG delta power during NREMS showed normal diurnal rhythms. The five-day experimental manipulation had significant effect on NREMS [ANOVA, day effect $F(5,55)=81.4$, $p<0.05$] and REMS [ANOVA, day effect $F(5,55)=77.2$, $p<0.05$]; these effects were different in WT and KO mice ANOVA, day x genotype interactions for NREMS $F(5,55)=11.3$, $p<0.05$; for REMS $F(5,55)=5.8$, $p<0.05$]. Similarly, body temperature and EEG SWA was also significantly altered during the experiment. Open symbols represent baseline day (plotted five times), whereas solid symbols represent experimental days. Data points represent 2-h averages. The horizontal bars for temp show periods of significant difference from baseline day (two-way ANOVA), and for NREMS and REMS show periods of significant difference between the baseline and experimental days (univariate tests of significance for planned comparison, $p<0.05$). Error bars show standard error. The gray shaded area shows the dark phase of the day. Asterisks indicate significant difference in body temperature or SWA between the baseline and experimental days (univariate tests of significance for planned comparison, $p<0.05$). Note the difference in the temperature y-scale between the cold days and the fasting/recovery days.

The thermoregulatory deficit in ghrelin KO mice was already apparent during the first three days of cold exposure when food was available ad libitum (FIG. 3A). Body temperatures were suppressed for the entire three-day period in ghrelin KO mice while near normal body temperature was maintained on cold days 2 to 3 in WT animals (FIG. 4A). Changes in sleep-wake activity paralleled those in body temperature. In ghrelin KO mice, NREMS was suppressed continuously for 72 h (FIG. 3B) while in WTs NREMS was normal during the light phases of the cold days (FIG. 4B). Also, in WT mice REMS completely normalized by the end of the first day (FIG. 4C), whereas REMS suppressions were evident for three days in KOs (FIG. 3C). According to particular aspects, the greater sleep suppression in ghrelin KO mice might reflect the activation of thermoregulatory compensatory mechanisms.

Applicants' observation of acute cold exposure suppression of sleep, EEG SWA and body temperature in all 4 genotypes confirms prior observations in cats (38), rats (39-41) and mice (42). Cold-suppressed REMS is followed by rebound increases if mice (42) or rats (43, 44) are returned to room temperature. Applicants observed similar rebound increases in REMS. In rats, acute cold suppressed EEG SWA is followed by rebound increases on the recovery day (43, 44) and in ground squirrels, EEG SWA is increased after hypothermic torpor bouts (45). In Applicants' animals, similar EEG SWA increases occurred on the recovery day. EEG SWA is often considered an indicator of NREMS intensity, and EEG SWA increases when sleep pressure is high, e.g., after sleep deprivation (46). Increased EEG SWA is semi-autonomous from actual sleep debt and may reflect altered brain activity after hypothermic periods (45, 47). Applicants' results are consistent with this interpretation because ghrelin KO animals lost 50% more sleep on the fasting day than the WTs, yet, rebound increases in EEG SWA were not different in the two genotypes.

Taken together, Applicants' results disclosed herein indicate that product(s) of the ghrelin gene have crucial roles in the physiological sleep and body temperature responses to metabolic challenge in mice, and for the first time define a physiologically relevant difference in phenotype between ghrelin KO and ghrelin receptor KO mice. The findings also provide further evidence for the coordinated regulation of metabolism and sleep.

Inhibition of Ghrelin Expression:

SiRNA. The siRNA molecules according to the present invention mediate RNA interference ("RNAi"). The term "RNAi" is well known in the art and is commonly understood to mean that the RNAis that can be used for inhibiting gene expression, including, for example, inhibition of one or more target genes in a cell by siRNA with a region which is complementary to the target gene. RNAi can occur by way of small interfering RNA (also called short interfering RNA or silencing) (siRNA), or microRNA (miRNA). (See, for example, U.S. Pat. No. 6,506,559; Milhavet et al., Pharm. Rev. 55:629-648, 2003; and Gitlin et al., J. Virol. 77:7159-7165, 2003; incorporated herein by reference). Various assays are known in the art to test siRNA for its ability to mediate RNAi (e.g., Elbashir et al., Methods 26:199-213, 2002). The effect of the siRNA according to the present invention on gene expression will typically result in expression of the target gene being inhibited by at least 10%, 33%, 50%, 90%, 95% or 99% when compared to a cell not treated with the RNA molecules according to the present invention.

"siRNA" or "small-interfering ribonucleic acid" according to the invention has the meanings known in the art, including the following aspects. The siRNA comprises two strands of ribonucleotides which hybridize along a complementary region under physiological conditions. The strands are separate but may optionally be joined by a molecular linker. Individual ribonucleotides may be unmodified naturally occurring ribonucleotides, unmodified naturally occurring deoxyribonucleotides or may be chemically modified or synthetic (see, e.g., WO/2007/128477, incorporated herein by reference).

In particular aspects, the siRNA molecules comprise a double-stranded region which is substantially identical to a region of the mRNA of the target gene. A region with 100% identity ("fully complementary") to the corresponding sequence of the target gene is preferred. However, the region may also contain one, two or three mismatches as compared to the corresponding region of the target gene, depending on the length of the region of the mRNA that is targeted, and as such is not necessarily fully complementary. In certain aspects, the siRNA molecules specifically target one given gene (only the desired target mRNA), and may have 100% homology to the target mRNA and, for example, at least 2 mismatched nucleotides to all other genes present in the cell or organism. Methods to identify and analyze siRNAs with sufficient sequence identity in order to effectively inhibit expression of a specific target sequence are known in the art; for example, sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group).

Another factor affecting the efficiency of the RNAi reagent is the target region of the target gene. As appreciated in the art, a suitable mRNA target region would be the coding region. Also suitable are untranslated regions, such as the 5'-UTR, the 3'-UTR, and splice junctions. The region of a target gene effective for inhibition by the RNAi reagent may be determined by routine experimentation. For instance, transfection assays as described in Elbashir S. M. et al, 2001 EMBO J., 20, 6877-6888 may be performed for this purpose. A number of other suitable assays and methods exist in the art which are well known to the skilled person.

In particular exemplary aspects, the length of the region of the siRNA complementary to the target, in accordance with the present invention, may be from 10 to 100 nucleotides, 12 to 25 nucleotides, 14 to 22 nucleotides or 15, 16, 17, 18, 19, 20 or 21 nucleotides. Where there are mismatches to the corresponding target region, the length of the complementary region will generally be somewhat longer than for fully complementary targets. Because the siRNA may carry overhanging ends (which may or may not be complementary to the target), or additional nucleotides complementary to itself but not the target gene, the total length of each separate strand of siRNA may be 10 to 100 nucleotides, 15 to 49 nucleotides, 17 to 30 nucleotides or 19 to 25 nucleotides.

The phrase "contacting a cell," and any derivations thereof as used herein, refers to methods of exposing a cell, delivering to a cell, or 'loading' a cell with an agent (e.g., siRNA agents, antisense agents, ribozyme agents, antibodies, etc) whether directly or indirectly by viral or non-viral vectors, and wherein such agent is bioactive upon delivery. The method of delivery will be chosen for the particular agent and use (e.g., reduction of appetite or food intake, reduction of body weight or treatment of obesity, reduction of body temperature or induction of hypothermia, etc.). Parameters that affect delivery, as is known in the medical art, can include, inter alia, the cell type affected (e.g. ghrelin producing cells), and cellular location.

Inhibition of gene expression refers to the absence (or observable decrease) in the level of protein and/or mRNA product from a gene target. Specificity refers to the ability to inhibit the target gene without manifest effects on other genes of the cell. The consequences of inhibition can be confirmed by examination of the outward properties of the cell or organism or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, fluorescence activated cell analysis (FACS), inhibition of ghrelin-mediated conditions as described herein. For RNA-mediated inhibition in a cell line or whole organism, gene expression is conveniently assayed by use of a reporter or drug resistance gene whose protein product is easily assayed. Many such reporter genes are known in the art.

The invention, in particular aspects, contemplates introduction of RNA with partial or fully double-stranded character into the cell or into the extracellular environment. According to the present invention, inhibition is specific to the particular cellular gene expression product (e.g., ghrelin, ghrelin/obestatin prepropeptide) in that a nucleotide sequence from a portion of the sequence is chosen to produce inhibitory RNA. This process is effective in producing inhibition (partial or complete), and is gene-specific. In particular embodiments, the target cell containing the siRNA or miRNA may be a mammalian cell, in vitro or in vivo. Methods of preparing and using siRNA or miRNA are generally disclosed in U.S. Pat. No. 6,506,559, incorporated herein by reference (see also reviews by Milhavet et al., *Pharmacological Reviews* 55:629-648, 2003; Gitlin et al., *J. Virol.* 77:7159-7165, 2003; and WO/2007/128477, incorporated herein by reference).

The siRNA may further comprise one or more strands of polymerized ribonucleotide, and may include modifications to either the phosphate-sugar backbone or the nucleoside, and may contain non-natural amino acids (e.g. amino acid analogs). The phosphodiester linkages of natural RNA may be modified to include at least one of a nitrogen or sulfur heteroatom. Modifications in RNA structure may be tailored to allow specific genetic inhibition while avoiding a general immune-based response in some organisms which is generated by dsRNA. Likewise, bases may be modified to block the activity of adenosine deaminase. RNA may be produced enzymatically or by partial/total organic synthesis, any modified ribonucleotide can be introduced by in vitro enzymatic or organic synthesis.

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses of double-stranded material may yield more effective inhibition. Inhibition is sequence-specific in that nucleotide sequences corresponding to the duplex region of the RNA are targeted for genetic inhibition. Nucleic acid containing a nucleotide sequence identical to a portion of the validated gene sequence is preferred for inhibition. RNA sequences with insertions, deletions, and single point mutations relative to the target sequence may also be effective for inhibition. Sequence identity may be optimized by alignment algorithms known in the art and calculating the percent difference between the nucleotide sequences. Alternatively, the duplex region of the RNA may be defined functionally as a nucleotide sequence that is capable of hybridizing with a portion of the target gene transcript.

RNA may be synthesized either in vivo or in vitro. Endogenous RNA polymerase of the cell may mediate transcription in vivo, or cloned RNA polymerase can be used for transcription in vivo or in vitro. For transcription from a transgene in vivo or an expression construct, a regulatory region may be used to transcribe the RNA strand (or strands).

For siRNA (RNAi or short hairpin RNA), the RNA may be directly introduced into the cell (i.e., intracellularly); or introduced extracellularly into a cavity, interstitial space, into the circulation of an organism, introduced orally, or may be introduced by bathing an organism in a solution containing RNA. Methods for oral introduction include direct mixing of RNA with food of the organism, as well as engineered approaches in which a species that is used as food is engineered to express an RNA, then fed to the organism to be affected.

Preferred siRNA compositions for oral delivery are chemically modified siRNA, as described in WO/2007/128477 (incorporated herein by reference), which confers a high in vivo stability suitable for oral delivery by including at least one modified nucleotide in at least one of the strands. Thus, the siRNA according to the present invention contains at least one modified or non-natural ribonucleotide. A description of many known chemical modifications are disclosed in WO 200370918 (incorporated by reference herein for such teachings on known chemical modifications). Suitable modifications include, but are not limited to modifications to the sugar moiety (i.e. the 2' position of the sugar moiety, such as for instance 2'-O-(2-methoxyethyl) or 2'-MOE) (Martin et al., Helv. Chim. Acta, 1995, 78, 486-504) i.e., an alkoxyalkoxy group) or the base moiety (i.e. a non-natural or modified base which maintains ability to pair with another specific base in an alternate nucleotide chain). Other modifications include so-called 'backbone' modifications including, but not limited to, replacing the phosphoester group (connecting adjacent ribonucleotides with for instance phosphorothioates, chiral phosphorothioates or phosphorodithioates). Finally, end modifications sometimes referred to herein as 3' caps or 5' caps may be of significance. As illustrated in Table 1 of WO/2007/128477, caps may consist of simply adding additional nucleotides, such as "T-T" which has been found to confer stability on an siRNA. Caps may consist of more complex chemistries which are known to those skilled in the art.

Delivery Methods for siRNA:

In certain embodiments, siRNAs are delivered to multi-organs using amphoteric, fully charge-reversible liposomes (Reinsch C. et al., Chapter 4: Drug & Gene Delivery Systems in Nanotechnology Vol. 2, p. 328-331, incorporated by reference herein for its disclosure and teachings relating to amphoteric, fully charge-reversible liposomes).

In further embodiments, siRNAs are introduced into target cells by cyclodextrin-containing polymers, as described in U.S. Pat. Nos. 7,270,808; 7,166,302; 7,091,192; 7,018,609; 6,884,789; and 6,509,323 (incorporated by reference herein for its disclosure and teachings relating to cyclodextrin-containing polymers). These polymers form the foundation for a two-part siRNA delivery system. The first component is a linear, cyclodextrin-containing polycation that, when mixed with small interfering RNA (siRNA), binds to the anionic "backbone" of the siRNA. The polymer and siRNA self-assemble into nanoparticles of approximately 50-80 nm diameter that fully protect the siRNA from nuclease degradation in serum. The siRNA delivery system has been designed to allow for intravenous injection. Upon delivery to the target cell, the targeting ligand binds to membrane receptors on the cell surface and the RNA-containing nanoparticle is taken into the cell by endocytosis. There, chemistry built into the polymer functions to unpackage the siRNA from the delivery vehicle. Both tumors and liver cells have been effectively targeted in vivo.

In certain embodiments, siRNA is delivered to target cells using hollow yeast cell wall particles (YCWP) (Aouadi, M., et al., Chapter 4: Drug & Gene Delivery Systems in Nanotechnology Vol. 2, p. 332-335, incorporated by reference herein for its disclosure and teachings relating to hollow yeast cell wall particles (YCWP)). The siRNAs are encapsulated within these hollow YCWP by in situ layer by layer synthesis of siRNA containing nanoplexes. YCWP provide for receptor-mediated oral bioavailability and macrophage targeting of nanoplexed cargos, such as siRNA. In further embodiments, these YCWP siRNA complexes are delivered to target cells via oral and intraperitoneal route.

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus the RNA may be introduced along with components that perform one or more of the following activities: enhance RNA uptake by the cell, promote annealing of the duplex strands, stabilize the annealed strands, or other-wise increase inhibition of the target gene.

RNA containing a nucleotide sequences identical to a portion of a particular gene sequence are preferred for inhibition. RNA sequences with insertions, deletions, and single point mutations relative to the target sequence may be effective for inhibition. Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of particular gene sequence is preferred. Alternatively, the duplex region of the RNA may be defined functionally as a nucleotide sequence that is capable of hybridizing with a portion of the particular gene transcript (e.g., 400 mM NaCl, 40 mM PIPES pH 6.4, 1 mM EDTA, 50° C. or 70° C. hybridization for 12-16 hours; followed by washing). Preferably, wherein the siRNA agent comprises a nucleic acid sequence of, e.g., at least 9, at least 15, at least 18, or at least 20 contiguous bases in length that is complementary to, or hybridizes under moderately stringent or stringent conditions to a sequence selected from the group consisting of SEQ ID NOS:1-6, and sequences complementary thereto.

A 100% sequence identity between the RNA and a particular gene sequence is not required to practice the present invention. Thus the methods have the advantage of being able to tolerate sequence variations that might be expected due to genetic mutation, strain polymorphism, or evolutionary divergence. Sequences with greater than about 90% identity, greater than about 91% identity, greater than about 92% identity, greater than about 93% identity, greater than about 94% identity, greater than about 95% identity, greater than about 96% identity, greater than about 97% identity, greater than about 98% identity, greater than about 99% identity, greater than about 99.5% identity, greater than about 99.9% identity, or any value there between may also be used with the present invention.

Particular gene sequence siRNA may be synthesized by art-recognized methods either in vivo or in vitro. Endogenous RNA polymerase of the cell may mediate transcription in vivo, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the RNA strand (or strands). Inhibition may be targeted by specific transcription in an organ, tissue, or cell type; stimulation of an environmental condition (e.g., infection, stress, temperature, chemical inducers); and/or engineering transcription at a developmental stage or age. The RNA strands may or may not be polyadenylated; the RNA strands may or may not be capable of being translated into a polypeptide by a cell's translational apparatus.

RNA may be chemically or enzymatically synthesized by manual or automated reactions. The RNA may be synthesized by a cellular RNA polymerase or a bacteriophage RNA polymerase (e.g., T3, T7, SP6). The use and production of an expression construct are known in the art (e.g., WO 97/32016; U.S. Pat. Nos. 5,593,874, 5,698,425, 5,712,135, 5,789,214, and 5,804,693; and the references cited therein). If synthesized chemically or by in vitro enzymatic synthesis, the RNA may be purified prior to introduction into the cell. For example, RNA can be purified from a mixture by extraction with a solvent or resin, precipitation, electrophoresis, chromatography, or a combination thereof. Alternatively, the RNA may be used with no or a minimum of purification to avoid losses due to sample processing. The RNA may be dried for storage or dissolved in an aqueous solution. The solution may contain buffers or salts to promote annealing, and/or stabilization of the duplex strands.

The siRNA may be used alone or as a component of a composition or kit having at least one of the reagents necessary to carry out the in vitro or in vivo introduction of RNA to test samples or subjects. Preferred components are the dsRNA and a vehicle that promotes introduction of the dsRNA. Such compositions and/or kits may also include instructions to allow a user of the composition or kit to practice the invention.

Further, one or more siRNA of the present invention may comprise a pharmaceutical or therapeutic composition that may be useful, for example, as an anti-obesity agent or a hypothermia-inducing agent. Such pharmaceutical or therapeutic compositions may further comprise inert ingredients, such as excipients, diluents, carriers, etc.

Downregulation of Ghrelin, Ghrelin/Obestatin Prepropeptide:

According to the present invention, inhibition is specific to the particular cellular gene expression product (e.g., ghrelin, ghrelin/obestatin prepropeptide) in that a nucleotide sequence from a portion of the sequence is chosen to produce inhibitory RNA. Several methods are available in the art to produce a silencing RNA molecule, i.e. an RNA molecule which when expressed reduces the expression of a particular gene or group of genes, including the so-called "sense" or "antisense" RNA technologies.

Antisense technology. Thus in one embodiment, the inhibitory RNA molecule encoding chimeric gene is based on the so-called antisense technology. In other words, the coding region of the chimeric gene comprises a nucleotide sequence of at least 19 or 20 consecutive nucleotides of the complement of the nucleotide sequence of the ghrelin, ghrelin/obestatin prepropeptide gene or an orthologue thereof. Such a chimeric gene may be constructed by operably linking a DNA fragment comprising at least 19 or 20 nucleotides from ghrelin, ghrelin/obestatin prepropeptide encoding gene or an orthologue thereof, isolated or identified as described elsewhere in this application, in inverse orientation to a plant expressible promoter and 3' end formation region involved in transcription termination and polyadenylation.

Co-suppression technology. In another embodiment, the inhibitory RNA molecule encoding chimeric gene is based on the so-called co-suppression technology. In other words, the coding region of the chimeric gene comprises a nucleotide sequence of at least 19 or 20 consecutive nucleotides of the nucleotide sequence of the ghrelin, ghrelin/obestatin prepropeptide encoding gene or an orthologue thereof. Such a chimeric gene may be constructed by operably linking a DNA fragment comprising at least 19 or 20 nucleotides from the ghrelin, ghrelin/obestatin prepropeptide encoding gene or an orthologue thereof, in direct orientation to a plant expressible promoter and 3' end formation region involved in transcription termination and polyadenylation.

The efficiency of the above mentioned chimeric genes in reducing the expression of the ghrelin, ghrelin/obestatin prepropeptide encoding gene or an orthologue thereof may be further enhanced by the inclusion of DNA element which result in the expression of aberrant, unpolyadenylated inhibitory RNA molecules or results in the retention of the inhibitory RNA molecules in the nucleus of the cells. One such DNA element suitable for that purpose is a DNA region encoding a self-splicing ribozyme, as described in WO 00/01133 (incorporated herein by reference in its entirety and particularly for its teachings on self-splicing ribozymes). Another such DNA element suitable for that purpose is a DNA region encoding an RNA nuclear localization or retention signal, as described in PCT/AU03/00292 published as WO03/076619 (incorporated by reference).

Double-stranded RNA (dsRNA) or interfering RNA (RNAi). A convenient and very efficient way of downregulating the expression of a gene of interest uses so-called double-stranded RNA (dsRNA) or interfering RNA (RNAi), as described e.g. in WO99/53050 (incorporated herein by reference in its entirety and particularly for its teachings on RNAi)). In this technology, an RNA molecule is introduced into a plant cell, whereby the RNA molecule is capable of forming a double stranded RNA region over at least about 19 to about 21 nucleotides, and whereby one of the strands of this double stranded RNA region is about identical in nucleotide sequence to the target gene ("sense region"), whereas the other strand is about identical in nucleotide sequence to the complement of the target gene or of the sense region ("antisense region"). It is expected that for silencing of the target gene expression, the nucleotide sequence of the 19 consecutive nucleotide sequences may have one mismatch, or the sense and antisense region may differ in one nucleotide. To achieve the construction of such RNA molecules or the encoding chimeric genes, use can be made of the vector as described in WO 02/059294.

Thus, in one embodiment of the invention, a method for regulating fatty acid unsaturation in seed oil, is provided comprising the step of introducing a chimeric gene into a cell of the plant, wherein the chimeric gene comprises the following operably linked DNA elements:
 (a) a plant expressible promoter;
 (b) a transcribed DNA region, which when transcribed yields a double-stranded RNA molecule capable of reducing specifically the expression of ghrelin, ghrelin/obestatin or an orthologue thereof, and the RNA molecule comprising a first and second RNA region wherein
  i) the first RNA region comprises a nucleotide sequence of at least 19 consecutive nucleotides having at least about 94% sequence identity to the nucleotide sequence of the ghrelin, ghrelin/obestatin gene or of an orthologue thereof;
  ii) the second RNA region comprises a nucleotide sequence complementary to the at least 19 consecutive nucleotides of the first RNA region;
  iii) the first and second RNA region are capable of base-pairing to form a double stranded RNA molecule between at least the 19 consecutive nucleotides of the first and second region; and (c) a 3' end region comprising transcription termination and polyadenylation signals functioning in cells of the plant.

The length of the first or second RNA region (sense or antisense region) may vary from about 19 nucleotides (nt) up to a length equaling the length (in nucleotides) of the endogenous gene involved in callose removal. The total length of the sense or antisense nucleotide sequence may thus be at least at least 25 nt, or at least about 50 nt, or at least about 100 nt, or at least about 150 nt, or at least about 200 nt, or at least about 500 nt. It is expected that there is no upper limit to the total length of the sense or the antisense nucleotide sequence. However for practical reasons (such as e.g. stability of the chimeric genes) it is expected that the length of the sense or antisense nucleotide sequence should not exceed 5000 nt, particularly should not exceed 2500 nt and could be limited to about 1000 nt.

It will be appreciated that the longer the total length of the sense or antisense region, the less stringent the requirements for sequence identity between these regions and the corresponding sequence in ghrelin, ghrelin/obestatin prepropeptide encoding gene and orthologues or their complements. Preferably, the nucleic acid of interest should have a sequence identity of at least about 75% with the corresponding target sequence, particularly at least about 80%, more particularly at least about 85%, quite particularly about 90%, especially about 95%, more especially about 100%, quite especially be identical to the corresponding part of the target sequence or its complement. However, it is preferred that the nucleic acid of interest always includes a sequence of about 19 consecutive nucleotides, particularly about 25 nt, more particularly about 50 nt, especially about 100 nt, quite especially about 150 nt with 100% sequence identity to the corresponding part of the target nucleic acid. Preferably, for calculating the sequence identity and designing the corresponding sense or antisense sequence, the number of gaps should be minimized, particularly for the shorter sense sequences.

dsRNA encoding chimeric genes according to the invention may comprise an intron, such as a heterologous intron, located e.g. in the spacer sequence between the sense and antisense RNA regions in accordance with the disclosure of WO 99/53050 (incorporated herein by reference).

Synthetic micro-RNAs (miRNAs). The use of synthetic micro-RNAs to downregulate expression of a particular gene in a plant cell, provides for very high sequence specificity of the target gene, and thus allows conveniently to discriminate between closely related alleles as target genes the expression of which is to be down-regulated.

Thus, in another embodiment of the invention, the biologically active RNA or silencing RNA or inhibitory RNA molecule may be a microRNA molecule, designed, synthesized and/or modulated to target and cause the cleavage ghrelin, ghrelin/obestatin prepropeptide encoding gene or an orthologue thereof in a plant. Various methods have been described to generate and use miRNAs for a specific target gene (including but not limited to Schwab et al. (2006, Plant Cell, 18(5): 1121-1133), WO2006/044322, WO2005/047505, EP 06009836, all incorporated herein by reference in their entirety, and particularly for their respective teachings relating to miRNA). Usually, an existing miRNA scaffold is modified in the target gene recognizing portion so that the generated miRNA now guides the RISC complex to cleave the RNA molecules transcribed from the target nucleic acid. miRNA scaffolds could be modified or synthesized such that the miRNA now comprises 21 consecutive nucleotides of the ghrelin, ghrelin/obestatin prepropeptide encoding nucleotide sequence or an orthologue thereof, such as the sequences represented in the Sequence listing, and allowing mismatches according to the herein below described rules.

Thus, in one embodiment, the invention provides a method for regulation of fatty acid unsaturation in seed oil comprising the steps of:

a. Introducing a chimeric gene into cells of an oilseed bearing plant, said chimeric gene comprising the following operably linked DNA regions:
  i. a plant expressible promoter;
  ii. a DNA region which upon introduction and transcription in a plant cell is processed into a miRNA, whereby the miRNA is capable of recognizing and guiding the cleavage of the mRNA of a ghrelin, ghrelin/obestatin prepropeptide encoding gene or an orthologue thereof of the plant; and
  iii. optionally, a 3' DNA region involved in transcription termination and polyadenylation.

The mentioned DNA region processed into a miRNA may comprise a nucleotide sequence which is essentially complementary to a nucleotide sequence of at least 21 consecutive nucleotides of a ghrelin, ghrelin/obestatin prepropeptide encoding gene or orthologue, provided that one or more of the following mismatches are allowed:

a. A mismatch between the nucleotide at the 5' end of the miRNA and the corresponding nucleotide sequence in the RNA molecule;
b. A mismatch between any one of the nucleotides in position 1 to position 9 of the miRNA and the corresponding nucleotide sequence in the RNA molecule; and/or
c. Three mismatches between any one of the nucleotides in position 12 to position 21 of the miRNA and the corresponding nucleotide sequence in the RNA molecule provided that there are no more than two consecutive mismatches.

As used herein, a "miRNA" is an RNA molecule of about 20 to 22 nucleotides in length which can be loaded into a RISC complex and direct the cleavage of another RNA molecule, wherein the other RNA molecule comprises a nucleotide sequence essentially complementary to the nucleotide sequence of the miRNA molecule whereby one or more of the following mismatches may occur:

d. A mismatch between the nucleotide at the 5' end of said miRNA and the corresponding nucleotide sequence in the target RNA molecule;
e. A mismatch between any one of the nucleotides in position 1 to position 9 of said miRNA and the corresponding nucleotide sequence in the target RNA molecule;
f. Three mismatches between any one of the nucleotides in position 12 to position 21 of said miRNA and the corresponding nucleotide sequence in the target RNA molecule provided that there are no more than two consecutive mismatches; and/or
g. No mismatch is allowed at positions 10 and 11 of the miRNA (all miRNA positions are indicated starting from the 5' end of the miRNA molecule).

A miRNA is processed from a "pre-miRNA" molecule by proteins, such as DicerLike (DCL) proteins, present in any plant cell and loaded onto a RISC complex where it can guide the cleavage of the target RNA molecules.

As used herein, a "pre-miRNA" molecule is an RNA molecule of about 100 to about 200 nucleotides, preferably about 100 to about 130 nucleotides which can adopt a secondary structure comprising a double stranded RNA stem and a single stranded RNA loop and further comprising the nucleotide sequence of the miRNA (and its complement sequence)

in the double stranded RNA stem. Preferably, the miRNA and its complement are located about 10 to about 20 nucleotides from the free ends of the miRNA double stranded RNA stem. The length and sequence of the single stranded loop region are not critical and may vary considerably, e.g. between 30 and 50 nt in length. Preferably, the difference in free energy between unpaired and paired RNA structure is between −20 and −60 kcal/mole, particularly around −40 kcal/mole. The complementarity between the miRNA and the miRNA* need not be perfect and about 1 to 3 bulges of unpaired nucleotides can be tolerated. The secondary structure adopted by an RNA molecule can be predicted by computer algorithms conventional in the art such as mFOLD. The particular strand of the double stranded RNA stem from the pre-miRNA which is released by DCL activity and loaded onto the RISC complex is determined by the degree of complementarity at the 5' end, whereby the strand which at its 5' end is the least involved in hydrogen bounding between the nucleotides of the different strands of the cleaved dsRNA stem is loaded onto the RISC complex and will determine the sequence specificity of the target RNA molecule degradation. However, if empirically the miRNA molecule from a particular synthetic pre-miRNA molecule is not functional (because the "wrong" strand is loaded on the RISC complex, it will be immediately evident that this problem can be solved by exchanging the position of the miRNA molecule and its complement on the respective strands of the dsRNA stem of the pre-miRNA molecule. As is known in the art, binding between A and U involving two hydrogen bounds, or G and U involving two hydrogen bounds is less strong that between G and C involving three hydrogen bounds.

Naturally occurring miRNA molecules may be comprised within their naturally occurring pre-miRNA molecules but they can also be introduced into existing pre-miRNA molecule scaffolds by exchanging the nucleotide sequence of the miRNA molecule normally processed from such existing pre-miRNA molecule for the nucleotide sequence of another miRNA of interest. The scaffold of the pre-miRNA can also be completely synthetic. Likewise, synthetic miRNA molecules may be comprised within, and processed from, existing pre-miRNA molecule scaffolds or synthetic pre-miRNA scaffolds.

The pre-miRNA molecules (and consequently also the miRNA molecules) can be conveniently introduced into a plant cell by providing the plant cells with a gene comprising a plant-expressible promoter operably linked to a DNA region, which when transcribed yields the pre-miRNA molecule. The plant expressible promoter may be the promoter naturally associated with the pre-miRNA molecule or it may be a heterologous promoter.

Dosage:

As used herein, "treatment" means an action taken to inhibit or reduce a process of a disease, disorder or condition, to inhibit or reduce a symptom of a disease, disorder or condition, or to prophylactically prevent the onset or further development of a disease, disorder or condition. "Treat" is the cognitive verb thereof.

An effective dose of the therapeutic agent of the invention is that dose required to treat a disease state. The effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.1 mg/kg and 100 mg/kg body weight/day of siRNA (or other RNA based agent) is administered dependent upon potency. The nucleic acid molecules of the invention and formulations thereof can be administered orally, topically, parenterally, by inhalation or spray, or rectally in dosage unit formulations containing conventional non-toxic pharmaceutically acceptable carriers, adjuvants and/or vehicles. The term parenteral as used herein includes percutaneous, subcutaneous, intravascular (e.g., intravenous), intramuscular, intraperitoneal, or intrathecal injection, or infusion techniques and the like. In addition, there is provided a pharmaceutical formulation comprising a nucleic acid molecule of the invention and a pharmaceutically acceptable carrier. One or more nucleic acid molecules of the invention can be present in association with one or more non-toxic pharmaceutically acceptable carriers and/or diluents and/or adjuvants, and if desired other active ingredients. The pharmaceutical compositions containing nucleic acid molecules of the invention can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable thr the manufacture of tablets. These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. Aqueous suspensions contain the active materials in a mixture with excipients suitable for the manufacture of aqueous suspensions.

Oral administration of the compositions of the invention include all standard techniques for administering substances directly to the stomach or gut, most importantly by patient controlled swallowing of the dosage form, but also by other mechanical and assisted means of such delivery.

Dosage levels of the order of from about 0.1 mg to about 140 mg per kilogram of body weight per day are useful in the treatments disclosed herein (about 0.5 mg to about 7 g per subject per day). The amount of active ingredient that can be combined with the carrier materials to produce a single dosage form varies depending upon the host treated and the particular mode of administration. Dosage unit forms generally contain between from about 1 mg to about 500 mg of an active ingredient. It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

Therapeutic effect of the therapeutic agents of the invention may be enhanced by combination with other agents. Typically such other agents will include agents known for use in treating or inducing similar conditions or diseases. Alternatively, such agents may be used to reduce side-effects or unwanted effects caused by the therapeutic agents of the invention.

Antibodies or Antibody Fragments

Agents of the present invention include antibodies and/or antibody fragments. Suitable antibodies may be monoclonal, polyclonal or humanized monoclonal antibodies. Antibodies may be derived by conventional hybridoma based methodology, from antisera isolated from validated protein inoculated animals or through recombinant DNA technology. Alternatively, inventive antibodies or antibody fragments may be identified in vitro by use of one or more of the readily available phage display libraries. Exemplary methods are disclosed herein.

In one embodiment of the present invention, antibody agents are monoclonal antibodies that may be produced as follows. Target proteins (e.g., obestatin) in a baculovirus based system. By this method, target protein cDNAs or epitope-bearing fragments thereof are ligated into a suitable plasmid vector that is subsequently used to transfect Sf9 cells to facilitate protein production. In addition, it may be advantageous to incorporate an epitope tag or other moiety to facilitate affinity purification of the target protein. Clones of Sf9 cells expressing a particular protein are identified, e.g., by enzyme-linked immunosorbant assay (ELISA), lysates are prepared and the target protein purified by affinity chromatography. The purified target protein is, for example, injected intraperitoneally, into BALB/c mice to induce antibody production. It may be advantageous to add an adjuvant, such as Freund s adjuvant, to increase the resulting immune response.

Serum is tested for the production of specific antibodies, and spleen cells from animals having a positive specific antibody titer are used for cell fusions with myeloma cells to generate hybridoma clones. Supernatants derived from hybridoma clones are tested for the presence of monoclonal antibodies having specificity against a particular validated protein or fragments thereof. For a general description of monoclonal antibody methodology, See, e.g., Harlow and Lane, Antibodies: A Laboratory Manual, Cold Spring Harbor Laboratory (1988).

In addition to the baculovirus expression system, other suitable bacterial or yeast expression systems may be employed for the expression of a particular target protein or polypeptides thereof. As with the baculovirus system, it may be advantageous to utilize one of the commercially available affinity tags to facilitate purification prior to inoculation of the animals. Thus, the target protein cDNA or fragment thereof may be isolated by, e.g., agarose gel purification and ligated in frame with a suitable tag protein such as 6-His, glutathione-S-transferase (GST) or other such readily available affinity tag. See, e.g., Molecular Biotechnology: Principles and Applications of Recombinant DNA, ASM Press pp. 160-161 (ed. Glick, B. R. and Pasternak, J. J. 1998).

In additional embodiments of the present invention, antibody agents are humanized anti-target protein monoclonal antibodies. The phrase humanized antibody refers to an antibody derived from a non-human antibody typically a mouse monoclonal antibody. Alternatively, a humanized antibody may be derived from a chimeric antibody that retains or substantially retains the antigen-binding properties of the parental, non-human, antibody but which exhibits diminished immunogenicity as compared to the parental antibody when administered to humans. The phrase chimeric antibody, as used herein, refers to an antibody containing sequence derived from two different antibodies (see, e.g., U.S. Pat. No. 4,816,567) which typically originate from different species. Most typically, chimeric antibodies comprise human and murine antibody fragments, generally human constant and mouse variable regions.

Because humanized antibodies are far less immunogenic in humans than the parental mouse monoclonal antibodies, they can be used for the treatment of humans with far less risk of anaphylaxis. Thus, these antibodies may be preferred in therapeutic applications that involve in vivo administration to a human such as, e.g., use as radiation sensitizers for the treatment of neoplastic disease or use in methods to reduce the side effects of, e.g., cancer therapy.

Humanized antibodies may be achieved by a variety of methods including, for example: (1) grafting the non-human complementarity determining regions (CDRs) onto a human framework and constant region (a process referred to in the art as humanizing), or, alternatively, (2) transplanting the entire non-human variable domains, but cloaking them with a human-like surface by replacement of surface residues (a process referred to in the art as veneering). In the present invention, humanized antibodies will include both humanized and veneered antibodies. These methods are disclosed in, e.g., Jones et al., Nature (1986) 321:522-525; Morrison et al., Proc. Natl. Acad. Sci., U.S.A., (1984) 81:6851-6855; Morrison and Oi, Adv. Immunol. (1988) 44:65-92; Verhoeyer et al., Science (1988) 239:1534-1536; Padlan, Molec. Immunol. (1991) 28:489-498; Padlan, Molec. Immunol. (1994) 31(3): 169-217; and Kettleborough, C. A. et al., Protein Eng. (1991) 4:773-83 each of which is incorporated herein by reference for their relevant teachings as used herein.

The phrase complementarity determining region refers to amino acid sequences which together define the binding affinity and specificity of the natural Fv region of a native immunoglobulin binding site. See, e.g., Chothia et al., J. Mol. Biol. (1987) 196:901-917; Kabat et al., U.S. Dept. of Health and Human Services NIH Publication No. 91-3242 (1991). The phrase constant region refers to the portion of the antibody molecule that confers effector functions. In the present invention, mouse constant regions are substituted by human constant regions. The constant regions of the subject humanized antibodies are derived from human immunoglobulins. The heavy chain constant region can be selected from any of the five isotypes: alpha, delta, epsilon, gamma or mu.

One method of humanizing antibodies comprises aligning the non-human heavy and light chain sequences to human heavy and light chain sequences, selecting and replacing the non-human framework with a human framework based on such alignment, molecular modeling to predict the conformation of the humanized sequence and comparing to the conformation of the parent antibody. This process is followed by repeated back mutation of residues in the CDR region which disturb the structure of the CDRs until the predicted conformation of the humanized sequence model closely approximates the conformation of the non-human CDRs of the parent non-human antibody. Such humanized antibodies may be further derivatized to facilitate uptake and clearance, e.g., via Ashwell receptors (see, e.g., U.S. Pat. Nos. 5,530,101 and 5,585,089, both incorporated herein by reference.

Humanized antibodies to a particular target protein can also be produced using transgenic animals that are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/10741 also discloses transgenic non-primate mammalian hosts capable of mounting an immune response to an immunogen, wherein the antibodies have primate constant and/or variable regions, and wherein the endogenous immunoglobulin-encoding loci are substituted or inactivated. WO 96/30498 discloses the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy claims, and express an exogenous immunoglobulin locus comprising one or more xenogeneic constant regions.

Using a transgenic animal described above, an immune response can be produced to a selected antigenic molecule (e.g., target protein or fragment thereof), and antibody-producing cells can be removed from the animal and used to produce hybridomas that secrete human monoclonal antibodies. Immunization protocols, adjuvants, and the like\ are known in the art, and are used in immunization of, for example, a transgenic mouse as described in WO 96/33735. This publication discloses monoclonal antibodies against a variety of antigenic molecules including IL-6, IL-8, TNF, human CD4, L-selectin, gp39, and tetanus toxin. The monoclonal antibodies can be tested for the ability to inhibit or neutralize the biological activity or physiological effect of the corresponding protein. WO 96/33735 discloses that monoclonal antibodies against IL-8, derived from immune cells of transgenic mice immunized with IL-8, blocked IL-8-induced functions of neutrophils. Human monoclonal antibodies with specificity for the antigen used to immunize transgenic animals are also disclosed in WO 96/34096.

For purposes of the present invention, target polypeptides and variants thereof are used to immunize a transgenic animal as described above. Monoclonal antibodies are made using methods known in the art, and the specificity of the antibodies is tested using isolated target polypeptides. The suitability of the antibodies for clinical use is tested by, for example, exposing HCMV-infected cells to the antibodies and measuring cell growth and/or phenotypic changes. Human monoclonal antibodies specific for a particular validated protein, or for a variant or fragment thereof can be tested for their ability to inhibit, for example, US28-mediated cell migration. Such antibodies would be suitable for pre-clinical and clinical trials as pharmaceutical agents for preventing or controlling HCMV-mediated effects, conditions or diseases.

It will be appreciated that alternative target protein inhibitor antibodies may be readily obtained by other methods commonly known in the art. One exemplary methodology for identifying antibodies having a high specificity for a particular validated protein is the phage display technology.

Phage display libraries for the production of high-affinity antibodies are described in, for example, Hoogenboom, H. R. et al., *Immunotechnology* (1998) 4(1):1-20; Hoogenboom, H. R., *Trends Biotechnol*. (1997) 15:62-70 and McGuinness, B. et al., *Nature* Bio. Technol. (1996) 14:1149-1154 each of which is incorporated herein by reference. Among the advantages of the phage display technology is the ability to isolate antibodies of human origin that cannot otherwise be easily isolated by conventional hybridoma technology. Furthermore, phage display antibodies may be isolated in vitro without relying on an animal s immune system.

Antibody phage display libraries may be accomplished, for example, by the method of McCafferty et al., *Nature* (1990) 348:552-554 which is incorporated herein by reference. In short, the coding sequence of the antibody variable region is fused to the amino terminus of a phage minor coat protein (pIII). Expression of the antibody variable region-pIII fusion construct results in the antibody s display on the phage surface with the corresponding genetic material encompassed within the phage particle.

A target protein, or fragment thereof suitable for screening a phage library may be obtained by, for example, expression in baculovirus Sf9 cells as described, supra. Alternatively, the target protein coding region may be PCR amplified using primers specific to the desired region of the validated protein. As discussed above, the target protein may be expressed in *E. coli* or yeast as a fusion with one of the commercially available affinity tags.

The resulting fusion protein may then be adsorbed to a solid matrix, e.g., a tissue culture plate or bead. Phage expressing antibodies having the desired anti-target protein binding properties may subsequently be isolated by successive panning, in the case of a solid matrix, or by affinity adsorption to a validated protein antigen column. Phage having the desired target protein inhibitory activities may be reintroduced into bacteria by infection and propagated by standard methods known to those skilled in the art. See, e.g., Hoogenboom, H. R., *Trends Biotechnol.*, supra for a review of methods for screening for positive antibody-pIII phage.

Example 1

In Response to the Combined Challenge of Low Environmental Temperature and Fasting, there was a Severe Thermoregulatory and Sleep Deficit in Ghrelin KO Animals But not in Ghrelin Receptor KO Mice or in Control Animals Used in these Studies Knock Out and Control Mice:

The sleep and thermoregulatory responses to the combined challenge of low environmental temperature and fasting in ghrelin KO (8), ghrelin receptor KO (growth hormone secretagogue receptor 1a (GHS-R1a)) mice (20) and respective control strains were determined in this working Example 1.

Methods:

After obtaining baseline body temperature and sleep-wake activity at 29±1° C. ambient temperatures, mice were exposed to reduced environmental temperature (17±1° C.) for three days. Water and food were available ad libitum during these days. On the fourth experimental day, cold exposure continued and food was removed from the animals' cages for 24 hours. At the end of the fasting, food was returned and ambient temperature was reset to baseline.

Results:

In response to the combined challenge of 17° C. temperature and 24-h fasting, there was a severe thermoregulatory and sleep deficit in the ghrelin KO animals but not in the ghrelin receptor KO mice or in the control animals used in these studies (FIG. 1).

FIGS. 1A and 1B shows the body temperature and the amount of total sleep time in ghrelin wild-type (WT; diamond symbols) and knockout (KO; open circle symbols) mice (FIG. 1A), and in ghrelin receptor WT and KO mice (FIG. 1B) during the day of fasting. Body temperature data are expressed as difference from baseline in 10-min averages. Body temperature was significantly different between ghrelin WT and ghrelin KO mice (ANOVA, genotype effect $F(1,13)=5.41$, $p<0.05$). By contrast, changes in body temperature were not significantly different between ghrelin receptor KO and WT mice (ANOVA, genotype effect $F(1,13)=2.4$, $p>0.05$). In FIG. 1A, the horizontal black bar with asterisk marks the period of significant difference between WT and KO mice (univariate tests of significance for planned comparison, p<0.05). The colors of symbols represent the amount of total sleep (expressed as % of recording time) during the 10-min periods. The horizontal grey bar at the bottom of the figures indicates the dark phase of the day period.

The deficit observed in the ghrelin KO mice was manifested as a precipitously declining body temperature to a near ambient level and the disappearance of electroencephalogram (EEG)-identifiable vigilance states.

Example 2

In Response to the Combined Challenge of Low Environmental Temperature and Fasting, the Correlation Between Time in Non-Rapid-Eye Movement Sleep (NREMS) and Body Temperature was Significantly Weaker in the Ghrelin KO Mice as Compared to Those Found in the Two Wild-Type (WT) and the Ghrelin Receptor KO Genotypes Knock Out and Control Mice:
See as above for Example 1.
Results:
In addition to the results of Example 1, the correlation between time in non-rapid-eye movement sleep (NREMS) and body temperature was significantly weaker in the ghrelin KO mice as compared to those found in the two wild-type (WT) and the ghrelin receptor KO genotypes (FIGS. 2A-2D).

FIGS. 2A-2D show, according to particular exemplary aspects, the correlation between the amount of non-rapid-eye movement sleep (NREMS) and body temperature during hours 1 to 16 on the baseline (open circles) and fasting days (closed circles) in ghrelin WT (FIG. 2A; left, top panel), ghrelin KO (FIG. 2B; left, bottom panel), ghrelin receptor WT (FIG. 2C; right, top panel) and ghrelin receptor KO (FIG. 2D; right, bottom panel) mice. Individual data points represent 10-min temperature (° C.) and NREMS (% of recording time) averages. The relatively weak correlation between body temperature and NREMS duration on the baseline day can be explained by the fact that, in addition to NREMS-related decreases in body temperature (35), there are also sleep-independent, circadian changes in temperature. In response to fasting in a cold environment, the correlation became significantly stronger and the regression line is shifted to the left in ghrelin WT, ghrelin receptor WT and KO mice. This reflects the fact that the hypothermic periods were associated with increases in NREMS but when body temperature was in the 36-37° C. range the dominant state was wakefulness. In ghrelin KO mice (FIG. 2B; left, bottom panel), the slope of regression line became significantly more horizontal on the fasting day [$F(1,188)=112.2$, $p<0.001$], indicating that the integrative mechanisms linking NREMS duration to body temperature are dependent upon the ghrelin gene. Multiple regression analyses revealed that the correlation between NREMS time and body temperature on the fasting day in ghrelin KO mice is significantly different from Ghrelin WT [$F(2,188)=148.3$, $p<0.001$], ghrelin receptor WT [$F(2,188)=166.2$, $p<0.001$] and ghrelin receptor KO mice [$F(2,188)=140.5$, $p<0.001$].

In the ghrelin KO mice, there were three distinct response phases to the cold and 24-h fasting challenge (FIG. 1).

During the first response phase, hours 1 to 6 of the fasting day, body temperature of ghrelin KO mice was normal but sleep was suppressed and NREMS became fragmented, in that both the number and the average duration of the episodes decreased (Table 1). Table 1 shows sleep parameters of ghrelin knockout (KO) and wild-type (WT) mice on the fasting day. Based on the characteristic changes in body temperature and sleep on the fasting day, body temperature, the amount of non-rapid-eye-movement sleep (NREMS) and rapid-eye-movement sleep (REMS), the total number and the average duration of NREMS and REMS bouts of ghrelin KO and WT mice were calculated for three time periods: Phase 1, hours 1-6; phase 2, hours 7-16; and phase 3, hours 17-24. Then data for each measurement were compared by using three-way ANOVA (genotype factor: independent measure, phase and day factors: repeated measures).

TABLE 1

Sleep parameters of ghrelin knockout (KO) and wild-type (WT) mice on the fasting day.

| | | WT | | KO | |
|---|---|---|---|---|---|
| | | Baseline day | Fasting day | Baseline day | Fasting day |
| Phase 1 Hours 1-6 | | | | | |
| $T_b$ | | 36.8 ± 0.2 | 37.2 ± 0.3 | 37.0 ± 0.2 | 36.7 ± 0.2 |
| Time in each vigilance states (min) | NREMS | 264.2 ± 25.9 | 52.3 ± 16.5 * | 268.3 ± 7.3 | 58.0 ± 20.1 * |
| | REMS | 23.5 ± 4.0 | 2.9 ± 1.2 * | 26.5 ± 3.2 | 5.2 ± 2.1 * |
| Average bout durations (min) | NREMS | 4.8 ± 0.4 | 5.2 ± 0.5 | 5.3 ± 0.3 | 2.2 ± 0.6 * $ |
| | REMS | 1.4 ± 0.2 | 1.6 ± 0.3 | 1.6 ± 0.1 | 0.9 ± 0.3 |
| Total number of bouts | NREMS | 34 ± 3.1 | 5.3 ± 1.5 * | 33.9 ± 1.9 | 13.6 ± 5.3 * |
| | REMS | 8.4 ± 1.5 | 1.3 ± 0.6 * | 9.1 ± 1.2 | 2.1 ± 0.8 * |
| Phase 2 Hours 7-16 | | | | | |
| $T_b$ | | 36.4 ± 0.2 | 34.7 ± 0.4 * | 36.7 ± 0.2 | 34.3 ± 0.5 * |
| Time in each vigilance states (min) | NREMS | 560.4 ± 16.7 | 499.5 ± 36.9 * | 576.6 ± 19.0 | 241.1 ± 38.3 $ * |
| | REMS | 55.4 ± 3.3 | 25.8 ± 4.3 * | 69.2 ± 4.2 | 11.5 ± 5.2 * |
| Average bout durations (min) | NREMS | 5.8 ± 0.6 | 11.9 ± 0.7 * | 6.4 ± 0.4 | 2.8 ± 0.3 $ * |
| | REMS | 1.5 ± 0.1 | 1.7 ± 0.2 | 1.6 ± 0.1 | 1.7 ± 0.5 |
| Total number of bouts | NREMS | 65.0 ± 5.8 | 29.0 ± 2.1 * | 60.5 ± 3.9 | 57.6 ± 9.3 $ |
| | REMS | 20.5 ± 1.6 | 8.9 ± 1.5 * | 26.4 ± 2.3 | 4.1 ± 1.9 * |

TABLE 1-continued

Sleep parameters of ghrelin knockout (KO) and wild-type (WT) mice on the fasting day.

|  |  | WT | | KO | |
|---|---|---|---|---|---|
|  |  | Baseline day | Fasting day | Baseline day | Fasting day |
| Phase 3 Hours 17-24 | | | | | |
| $T_b$ | | 36.1 ± 0.2 | 35.1 ± 0.2 | 36.3 ± 0.2 | 28.4 ± 0.6 $ * |
| Time in each vigilance states (min) | NREMS | 463.1 ± 15.0 | 264.9 ± 48.5 * | 489.4 ± 11.9 | 18.6 ± 7.4 $ * |
| | REMS | 49.7 ± 2.4 | 18.9 ± 4.7 * | 65.0 ± 4.9 $ | 0.2 ± 0.1 $ * |
| Average bout durations (min) | NREMS | 6.0 ± 0.6 | 8.8 ± 1.2 * | 6.7 ± 0.3 | 2.8 ± 0.5 $ * |
| | REMS | 1.6 ± 0.1 | 1.8 ± 0.2 | 1.8 ± 0.1 | N/A |
| Total number of bouts | NREMS | 51.8 ± 4.4 | 18.1 ± 2.8 * | 49.6 ± 2.2 | 4.6 ± 2.0 $ * |
| | REMS | 18.6 ± 1.3 | 6.0 ± 1.4 * | 22.7 ± 1.4 | 0.1 ± 0.1 * |

* significant difference from baseline,
$ significant difference between WT and KO mice.

In the second response phase (h 7-16), ghrelin KO mice showed hypothermic bouts with their body temperature 2-4° C. below baseline and severely suppressed, highly fragmented sleep.

During the third response phase, beginning from about hour 17, body temperature of the ghrelin KO mice started to decrease precipitously and reached 23.3±1.0° C. by the end of the day. During this hypothermic period NREMS was suppressed to 4% of baseline and rapid-eye movement sleep (REMS) almost completely disappeared, only two animals showed one single short episode of REMS. When the body temperature of an individual animal dropped below ~30° C., the amplitude of the EEG signal started to decrease and it was not possible to distinguish sleep and wake stages by using the conventional criteria; these periods were scored as an undefined vigilance state. In the last three hours of the fasting day none of the ghrelin KO mice had distinguishable NREMS and REMS bouts. This EEG phenotype was not observed in any other genotypes used, including the ghrelin receptor KO mice. There was no evidence of spontaneous arousal in ghrelin KO mice during the third phase.

On the recovery day, when cage temperature was increased back to 30° C. and food was returned, two of the ghrelin KO animals did not show any increase in body temperature or any EEG or behavioral signs of recovery. These mice were removed from the cage after one hour and were rewarmed under an infrared lamp. The body temperature of most of the animals gradually rose on the recovery day and reached normal values within 5-6 hours. Thereafter temperature increased above baseline for the rest of the day (FIG. 3A). Parallel to the rise in body temperature, the amplitude of the EEG signal also increased and normal EEG returned by the end of the first hour in each surviving animal. REMS showed rebound increases during the dark period of the recovery day. EEG slow-wave activity (SWA) was significantly elevated during the first half of the night then returned to normal level.

Specifically, FIGS. 3A-3C show, according to particular exemplary aspects, body temperature FIG. 3A; top panel), non-rapid-eye-movement sleep (NREMS) (FIG. 3B; middle panel), slow wave activity (FIG. 3B; SWA inserts), and rapid-eye-movement sleep (REMS) (FIG. 3C; bottom panel) of ghrelin KO mice during the course of the experiments of Examples 1 and 2 herein. On the baseline day, body temperature, NREMS, REMS and EEG delta power during NREMS showed normal diurnal rhythms. The five-day experimental manipulation had significant effect on NREMS [ANOVA, day effect F(5,55)=81.4, p<0.05] and REMS [ANOVA, day effect F(5,55)=77.2, p<0.05]; these effects were different in WT and KO mice ANOVA, day x genotype interactions for NREMS F(5,55)=11.3, p<0.05; for REMS F(5,55)=5.8, p<0.05]. Similarly, body temperature and EEG SWA was also significantly altered during the experiment. Open symbols represent baseline day (plotted five times), whereas solid symbols represent experimental days. Data points represent 2-h averages. The horizontal bars for temperature (FIG. 3A) show periods of significant difference from baseline day (two-way ANOVA), and for NREMS (FIG. 3B) and REMS (FIG. 3C) show periods of significant difference between the baseline and experimental days (univariate tests of significance for planned comparison, p<0.05). Error bars show standard error. The gray shaded area shows the dark phase of the day. Asterisks indicate significant difference in body temperature or SWA between the baseline and experimental days (univariate tests of significance for planned comparison, p<0.05). Note the difference in the temperature y-scale between the cold days and the fasting/recovery days.

FIGS. 4A-4C show, according to particular exemplary aspects, body temperature (FIG. 4A), NREMS, SWA (FIG. 4B) and REMS (FIG. 4C) of ghrelin WT mice during the course of the experiments of FIGS. 1-3. Experimental manipulations induced significant changes in body temperature and sleep of ghrelin WT mice. The direction of these changes was similar to those seen in KOs. Open symbols represent baseline day (plotted five times), whereas solid symbols represent experimental days. Data statistics and details were as described in relation to the data of FIGS. 1 and 3.

The first response phase on the fasting day in WT mice was similar to those seen in ghrelin KOs. Body temperature was normal but NREMS and REMS were suppressed to 20% and 11% of the baseline, respectively. These reductions were due to the decrease in the number of sleep episodes (Table 1). In the second phase, between hours 7-16, body temperature declined reaching 32.7±1.5° C. by the end of the dark phase. Mice exhibited several hypothermic bouts of 1-5° C. (FIGS. 1 and 4). Increases in sleep were apparent during these bouts which led to an overall increase in sleep as compared to the first phase but still remained below baseline (90 and 47% of the baseline amounts for NREMS and REMS, respectively). The duration of individual NREMS episodes increased two-fold above baseline indicating enhanced sleep consolidation (Table 1). During the third response phase (h 17-24), there was a second decline in sleep while body temperature gradually returned towards normal. This sleep decrease was due to a drop in the number of sleep episodes but NREMS remained highly consolidated, i.e., the average duration of NREMS bouts was still increased compared to baseline (Table 1). Body temperature and sleep returned to normal on the recovery day. EEG SWA was increased for 6 h at the beginning of the recovery day.

There were already signs of impaired cold tolerance of ghrelin KO animals on the cold exposure days preceding the fasting (FIGS. 3A-3C). While cold exposure suppressed body temperature, REMS and EEG SWA only on the first cold exposure day in WT mice (FIG. 4), in ghrelin KO animals body temperature and NREMS were suppressed for the entire duration of the three-day cold exposure. The amount of NREMS was reduced on the first cold day and only during the nights of the subsequent cold days in the WTs. REMS did not show any significant difference from baseline during the cold days 2 and 3 in WT mice but was suppressed on cold day 1 and during the lights phases of cold days 2 and 3 in ghrelin KO animals.

Figure 5:
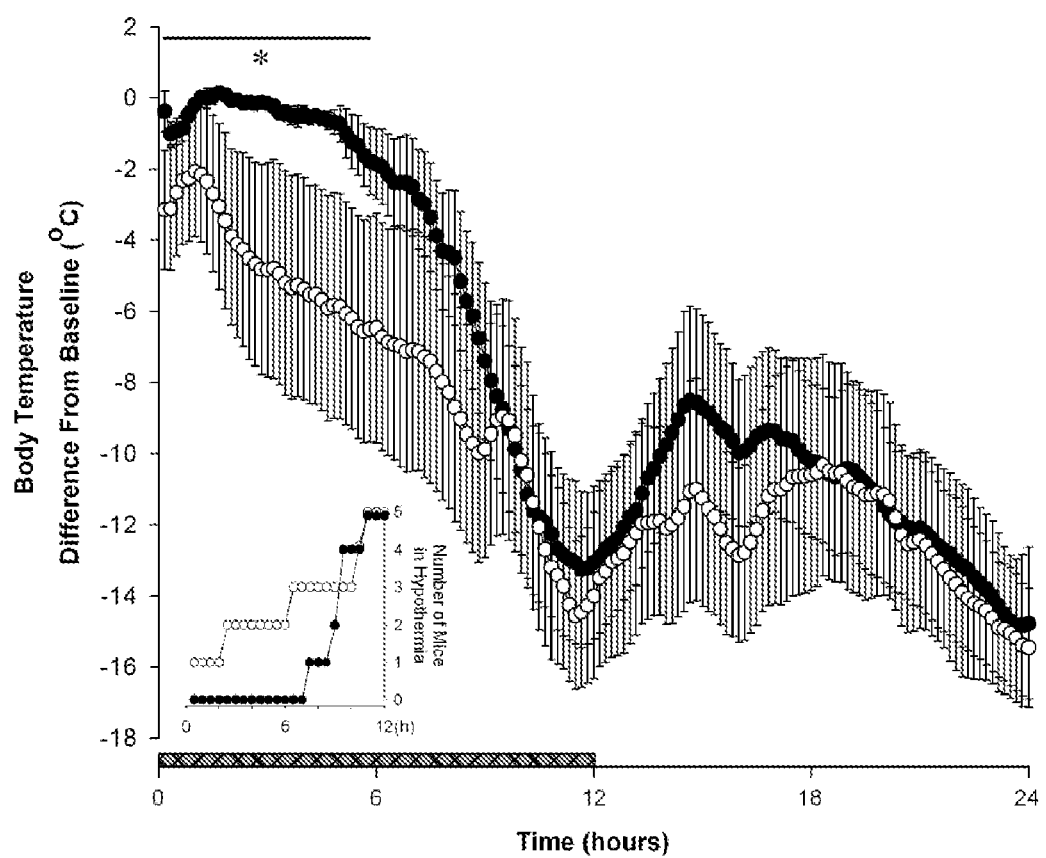
FIG. 5 shows, according to particular exemplary aspects, body temperature after saline (open symbols) or obestatin (solid symbols) delivery by osmotic minipumps in ghrelin KO mice during the fasting day. Body temperature data are expressed as difference from baseline in 10-min averages. Body temperature was significantly different between saline- and obestatin-treated mice during the first 6 hours of the fasting day, as shown by the period corresponding to the horizontal black bar with asterisk, showing a significant difference between saline- and obestatin-treated mice (two-way ANOVA for repeated measures, repeated factor: time, independent factor: treatment, treatment x time interaction $F(35, 490)=1.52$, $p<0.05$)). The horizontal grey bar shows the dark phase of the day. The figure inset shows the number of mice with body temperature 12° C. or more below baseline during the first 12-hour of the fasting day (saline treatment: open symbols, obestatin treatment: solid symbols).

The responses of ghrelin receptor KO mice to cold or the combination of cold and fasting were not significantly different from their own WT controls and from the WT controls of the ghrelin KO mice (FIG. 1 and Table 2).

the development of hypothermia in ghrelin KO mice on the fasting day (FIG. 5). Mice that received subcutaneous infusion of 300 nmol/kg/day obestatin for 10 days entered hypothermia about 6 hours later that those received saline.

Specifically, FIG. 5 shows, according to particular exemplary aspects, body temperature after saline (open symbols) or obestatin (solid symbols) delivery by osmotic minipumps in ghrelin KO mice during the fasting day. Body temperature data are expressed as difference from baseline in 10-min averages. Body temperature was significantly different between saline- and obestatin-treated mice during the first 6 hours of the fasting day, as shown by the period corresponding to the horizontal black bar with asterisk, showing a significant difference between saline- and obestatin-treated mice (two-way ANOVA for repeated measures, repeated factor: time, independent factor: treatment, treatment x time interaction $F(35,490)=1.52$, $p<0.05$)). The horizontal grey bar shows the dark phase of the day. The figure inset shows the number of mice with body temperature 12° C. or more below baseline during the first 12-hour of the fasting day (saline treatment: open symbols, obestatin treatment: solid symbols).

TABLE 2

Body temperature, the amount of NREMS and REMS of ghrelin receptor KO and WT mice during the three phases of the fasting day (See discussion for Table 1 above for details).

| | | WT | | KO | |
|---|---|---|---|---|---|
| | | Baseline day | Fasting day | Baseline day | Fasting day |
| Phase 1 (Hours 1-6) | | | | | |
| $T_b$ | | 37.3 ± 0.1 | 37.1 ± 0.1 | 37.5 ± 0.1 | 37.5 ± 0.1 |
| Time in each vigilance states (min) | NREMS | 195.1 ± 17.1 | 64.8 ± 26.3* | 176.1 ± 10.3 | 59.9 ± 17.5* |
| | REMS | 12.1 ± 1.7 | 2.3 ± 1.3* | 11.9 ± 1.6 | 2.1 ± 0.9* |
| Phase 2 (Hours 7-16) | | | | | |
| $T_b$ | | 36.8 ± 0.1 | 35.2 ± 0.4* | 37.0 ± 0.1 | 35.6 ± 0.2* |
| Time in each vigilance states (min) | NREMS | 516.8 ± 19.0 | 407.6 ± 23.0* | 476.3 ± 11.8 | 383.8 ± 18.0* |
| | REMS | 57.9 ± 2.8 | 18.4 ± 5.2* | 56.6 ± 5.7 | 32.6 ± 5.8* |
| Phase 3 (Hours 17-24) | | | | | |
| $T_b$ | | 36.0 ± 0.1 | 35.4 ± 0.2* | 36.4 ± 0.1 | 35.4 ± 0.2* |
| Time in each vigilance states (min) | NREMS | 488.7 ± 5.9 | 281.4 ± 65.7* | 469.7 ± 6.8 | 376.5 ± 25.3 |
| | REMS | 64.6 ± 3.7 | 26.7 ± 7.6* | 68.0 ± 3.4 | 41.3 ± 6.4* |

Example 3

Replacement of Obestatin Using Osmotic Minipump Significantly Attenuated the Development of Hypothermia in Ghrelin KO Mice on the Fasting Day Knock Out and Control Mice:
See as above for Examples 1 and 2.
Results:
In addition to the results of Examples 1 and 2, replacement of obestatin using osmotic minipump significantly attenuated Example 4

Oral Delivery of Ghrelin siRNA for Suppressing Food Intake in Rats

In certain preferred embodiments, baseline food intake for the 12-h light and dark period is measured over a 48-h time period in rats (n=16) that receive no treatment. On the third day, rats are separated randomly into two groups. One group of rats (n=8) is treated with scrambled ghrelin siRNA, the other group of rats receive ghrelin siRNA in the same volume administered orally by using an intragastric gavage. The dose and the specific siRNA is determined by an initial screening of ghrelin siRNAs using cultured cells. The siRNA that induces a significant suppression of ghrelin mRNA (for example, Applicants have shown that GGUUCAAUGCUC-CCUUCGAtt (SEQ ID NO:17) suppressed ghrelin mRNA levels by 40% in vitro) compared to scrambled or saline control is, then, used in vivo. Food intake is measure before dark and light onset on each experimental day and for 5 additional days after the siRNA treatment. Body weight is monitored once a day. Additionally, rats are implanted with EEG and EMG electrodes for sleep-wake recordings.

In further preferred embodiments, oral delivery of ghrelin siRNA, but not the scrambled siRNA suppresses food intake in rats. According to additional aspects, the effects of siRNAs in vivo are reversible; they begin about 1 day after administration and last 2-3 days. In further preferred aspects, the feeding suppressing effect of ghrelin siRNA diminishes by the end of the 5$^{th}$ day.

Example 5

Oral Delivery of Ghrelin siRNA for Suppressing Body Weight in Rats

According to certain aspects, baseline food intake for the 12-h light and dark period is measured over a 48-h time period in rats (n=16) that receive no treatment. On the third day, rats are separated randomly into two groups. One group of rats (n=8) is treated with scrambled ghrelin siRNA, the other group of rats receive ghrelin siRNA in the same volume administered orally by using an intragastic gavage. The dose and the specific siRNA is determined by an initial screening of ghrelin siRNAs using cultured cells. The siRNA that induces a significant suppression of ghrelin mRNA compared to scrambled or saline control is, then, used in vivo. The ghrelin siRNA treatment continues for three weeks. According to certain aspect, rats are treated with ghrelin siRNA on every third or fourth day. Food intake, separately for the dark and light period and body weight of each rat is measured on each experimental day. Additionally, rats are implanted with EEG and EMG electrodes for sleep-wake recordings.

In further embodiments, oral delivery of ghrelin siRNA over a long time period significantly suppresses food intake and body weight in rats.

Example 6

Oral Delivery of Ghrelin siRNA for Suppressing Body Weight in Obese Rats

According to certain aspects, baseline food intake for the 12-h light and dark period is measured over a 48-h time period in obese rats (n=16) that receive no treatment. On the third day, the obese rats are separated randomly into two groups. One group of obese rats (n=8) is treated with scrambled ghrelin siRNA, the other group of obese rats receive ghrelin siRNA in the same volume administered orally by using an intragastic gavage. The dose and the specific siRNA is determined by an initial screening of ghrelin siRNAs using cultured cells. The siRNA that induces a significant suppression of ghrelin mRNA compared to scrambled or saline control is, then, used in vivo. The ghrelin siRNA treatment continues for three weeks. According to certain aspect, obese rats are treated with ghrelin siRNA on every third or fourth day. Food intake, separately for the dark and light period and body weight of each obese rat is measured on each experimental day. Additionally, rats are implanted with EEG and EMG electrodes for sleep-wake recordings.

In further preferred embodiments, oral delivery of ghrelin siRNA over a long time period significantly suppresses food intake and body weight in obese rats.

Example 7

Obestatin Antibody Treatment for Reducing Body Temperature in Rats

In certain embodiments, two group of rats (n=8 for each group) are implanted with wax-coated temperature sensitive transmitters in the abdominal cavity. Baseline body temperature, food intake and body weight are recorded from the beginning of the dark phase at thermoneutral ($23\pm1°$ C.) ambient temperature. After baseline recordings, ambient temperature is reduced to $17\pm1°$ C. for three days. On the fourth day, cold exposure is continued and food is removed from the cages and saline or obestatin antibody (the effective dose is determined in a pilot study) is injected at the beginning of dark phase. After 24 hours, ambient temperature will be reset to $23\pm1°$ C., and food is returned to the animals. Additionally, rats are implanted with EEG and EMG electrodes for sleep-wake recordings.

According to additional aspects, the Obestatin antibody induces a significant decrease in body temperature in response to food deprivation in a cold environment in rats that can be reversed by resetting the baseline conditions.

Example 8

Oral Delivery of Obestatin siRNA for Reducing Body Temperature in Rats

According to additional aspects, baseline body temperature rhythm will be recorded over a 48-h time period in rats (n=16) that receive no treatment and kept at thermoneutral ($23\pm1°$ C.) or at ambient temperature. On the third day, rats are separated randomly into two groups. One group is treated with scrambled obestatin siRNA; the other group of rats receives obestatin siRNA in the same volume, administered orally by using an intragastic gavage. The dose and the specific siRNA is determined by an initial screening of obestatin siRNAs using cultured cells. The obestatin siRNA that induces a significant suppression of obestatin mRNA compared to scrambled or saline control is, then, used in vivo. Body temperature is recorded throughout the experiment day and for 5 additional days after the siRNA treatment. Additionally, rats are implanted with EEG and EMG electrodes for sleep-wake recordings.

According to further aspects, baseline body temperature rhythm is recorded over a 48-h time period in rats (n=16) that receive no treatment and kept at thermoneutral ($23\pm1°$ C.) or at ambient temperature. On the third day, the ambient temperature is lowered to $17\pm1°$ C. and rats are separated randomly into two groups. One group is treated with scrambled obestatin siRNA; the other group of rats receives obestatin siRNA in the same volume, administered orally by using an intragastic gavage. The dose and the specific siRNA is determined by an initial screening of obestatin siRNAs using cultured cells. The obestatin siRNA that induces a significant suppression of obestatin mRNA compared to scrambled or saline control is, then, used in vivo. Body temperature is recorded throughout the experiment day and for 5 additional days after the siRNA treatment.

According to additional aspects, baseline body temperature rhythm will be recorded over a 48-h time period in rats (n=16) that receive no treatment and kept at thermoneutral (23±1° C.) or at ambient temperature. On the third day, the ambient temperature is lowered to 17±1° C., rats are separated randomly into two groups and deprived of food. One group is treated with scrambled obestatin siRNA; the other group of rats receives obestatin siRNA in the same volume, administered orally by using an intragastic gavage. The dose and the specific siRNA is determined by an initial screening of obestatin siRNAs using cultured cells. The obestatin siRNA that induces a significant suppression of obestatin mRNA compared to scrambled or saline control is, then, used in vivo. Body temperature is recorded throughout the experiment day and for 5 additional days after the siRNA treatment. Additionally, rats are implanted with EEG and EMG electrodes for sleep-wake recordings.

According to further aspects, obestatin siRNA treatment (with or without the challenge of cold ambient temperature and food deprivation) but not the scrambled siRNA, suppresses body temperature in rats.

Accordingly, particular disclosed embodiments provide additional information and novel approaches for translational medicine to improve human and animal health. Further embodiments provide new, orally active drugs that suppress food intake and body weight.

Certain embodiments provide for regulated hypothermia having substantial utility for decreasing metabolism during prolonged surgeries, preserving organs before transplantation and improving survival of humans during trauma. For example, according to particular aspects, hypothermia during reperfusion during cardiac arrest significantly improves functional recovery.

Example 9

Exemplary siRNA Sequences

According to further rat and murine aspects, examples of the siRNA sequences (5'-3') that are used in the above experiments are shown in Table 3, along with sequences complementary thereto or a portion thereof.

TABLE 3

Preferred reagents for practicing the invention in rats and mice are SEQ ID NOS: 13-17 and their complementary sequences or a portion thereof.

| ghrelin siRNA (animal model) | SEQ IN NO |
|---|---|
| AGCUGUCAGGAGCUCAGUAtt (rat) | SEQ ID NO: 13 |
| GGAAAGUUUCUUCAGGAUAtt (rat) | SEQ ID NO: 14 |
| GGAGCUGGAAAUCAGGUUCtt (rat) | SEQ ID NO: 15 |
| AGGCGCCAGCUGACAAGUAtt (mouse) | SEQ ID NO: 16 |
| GGUUCAAUGCUCCCUUCGAtt (mouse) | SEQ ID NO: 17 |

Example 10

Exemplary Oligonucleotide Sequences

According to further human treatment aspects and with respect to human siRNA reagents, examples of inventive oligonucleotide sequences of length X (in nucleotides), as indicated by polynucleotide positions with reference to, for example, SEQ ID NO:1, include those corresponding to sets (sets corresponding to both the sense and antisense sequences of SEQ ID NO:1) of consecutively overlapping oligonucleotides of length X, where the oligonucleotides within each consecutively overlapping set (corresponding to a given X value) are defined as the finite set of Z oligonucleotides from nucleotide positions:

n to (n+(X-1));

where n=1, 2, 3, . . . (Y-(X-1));

where Y equals the length (nucleotides or base pairs) of SEQ ID NO:1 (354);

where X equals the common length (in nucleotides) of each oligonucleotide in the set (e.g., X=19 for a set of consecutively overlapping 19-mers); and where the number (Z) of consecutively overlapping oligomers of length X for a given SEQ ID NO of length Y is equal to Y-(X-1). For example Z=354-18=337 for either sense or antisense sets of SEQ ID NO:1, where X=19.

Examples of inventive 19-mer oligonucleotides include the following set of 336 oligomers (and the antisense set complementary thereto), indicated by polynucleotide positions with reference to SEQ ID NO:1:

1-19, 2-20, 3-21, 4-22, 5-23, . . . and 336-354.

Likewise, examples of inventive 25-mer oligonucleotides include the following set of 330 oligomers (and the antisense set complementary thereto), indicated by polynucleotide positions with reference to SEQ ID NO:1:

1-25, 2-26, 3-27, 4-28, 5-29, . . . and 330-354.

The present invention encompasses, for each of SEQ ID NO:1 to 6 (sets corresponding to both the sense and antisense sequences of SEQ ID NO:1-6), multiple consecutively overlapping sets of oligonucleotides or modified oligonucleotides of length X, where, for example, X=9, 10, 11, 12, 13, 14, 15, 16, 17, 18, 19, 20, 21, 22, 23, 24, 25, 26, 27, 28, 29, 30 or greater (e.g., 35 nucleotides in length).

The oligonucleotides or oligomers or siRNA agents according to the present invention provide for practicing the disclosed methods. Preferred sets of such oligonucleotides or modified oligonucleotides of length X are those consecutively overlapping sets of oligomers corresponding to SEQ ID NO:1 to SEQ ID NO:6 (and to the complements thereof).

Exemplary Homo sapiens Ghrelin/Obestatin Sequences:

Homo sapiens ghrelin/obestatin prepropeptide (GHRL), transcript variant 1, mRNA and proteins (aa 24-51, and 76-98):

NM_016362
(SEQ ID NO: 1)
atgccctccc cagggaccgt ctgcagcctc ctgctcctcg gcatgctctg gctggacttg gccatggcag gctccagctt cctgagccct gaacaccaga gagtccagca gagaaaggag tcgaagaagc caccagccaa gctgcagccc cgagctctag caggctggct ccgcccggaa gatggaggtc aagcagaagg ggcagaggat gaactggaag tccggttcaa cgcccccttt gatgttggaa tcaagctgtc aggggttcag taccagcagc acagccaggc cctggggaag tttcttcagg acatcctctg ggaagaggcc aaagaggccc cagccgacaa gtga NP_057446
(SEQ ID NO: 7)
mpspgtvcsl lllgmlwldl ama<u>gssflsp</u> <u>ehqrvqqrke</u>

<u>skkppaklqp</u> <u>r</u>alagwlrpe dggqaegaed elevrfnapf

<u>dvqiklsqvq</u> <u>yqqhsqalg</u>k flqdilweea keapadk

*Homo sapiens* ghrelin/obestatin prepropeptide (GHRL), transcript variant 2, mRNA and proteins (aa 24-50, and 75-97):

```
NM_001134941
                                           (SEQ ID NO: 2)
atgccctccc cagggaccgt ctgcagcctc ctgctcctcg gcatgctctg gctggacttg gccatggcag gctccagctt cctgagccct gaacaccaga gagtccagag aaaggagtcg aagaagccac cagccaagct gcagcccga gctctagcag gctggctccg cccggaagat ggaggtcaag cagaaggggc agaggatgaa ctggaagtcc ggttcaacgc ccccttttgat gttggaatca agctgtcagg ggttcagtac cagcagcaca gccaggccct ggggaagttt cttcaggaca tcctctggga agaggccaaa gaggcccag ccgacaagtg a NP_001128413
                                           (SEQ ID NO: 8)
mpspgtvcsl lllgmlwldl amaqssflsp ehqrvqrkes kkppaklqpr alagwlrped ggqaegaede levrfnapfd vqiklsqvqy qqhsqalgkf lqdilweeak eapadk
```

*Homo sapiens* ghrelin/obestatin prepropeptide (GHRL), transcript variant 3, mRNA and proteins (aa -----, and 64-86):
Transcript Variant: This variant (3) is generated from a more distal promoter, includes an alternate first exon which contains an upstream in-frame AUG codon, and omits an in-frame coding exon compared to variant 1. The resulting isoform (3) has a shorter and distinct N-terminus, as compared to isoform 1. Isoform 3 includes the obestatin ligand.

```
NM_001134944
                                           (SEQ ID NO: 3)
atgtttactt gctggtggtc ttatctaaga tcaacattgg cagctgtgcc cggagaggcc tccagggtcc agcagagaaa ggagtcgaag aagccaccag ccaagctgca gccccgagct ctagcaggct ggctccgccc ggaagatgga ggtcaagcag aaggggcaga ggatgaactg gaagtccggt tcaacgcccc ctttgatgtt ggaatcaagc tgtcagggt tcagtaccag cagcacagcc aggccctggg gaagtttctt caggacatcc tctgggaaga ggccaaagag gccccagccg acaagtga NP_001128416
                                           (SEQ ID NO: 9)
mftcwwsylr stlaavpgea srvqqrkesk kppaklqpra lagwlrpedg gqaegaedel evrfnapfdv qiklsqvqyq qhsqalgkfl qdilweeake apadk
```

*Homo sapiens* ghrelin/obestatin prepropeptide (GHRL), transcript variant 4, mRNA and proteins (aa -----, and 63-85):
Transcript Variant: This variant (4) is generated from a more distal promoter, includes an alternate first exon which contains an upstream in-frame AUG codon, and omits an in-frame coding exon compared to variant 1. An alternate splice acceptor site is used in the CDS resulting in the omission of 3 nt. The resulting isoform (4) has a shorter and distinct N-terminus, as compared to isoform 1. Isoform 4 includes the obestatin ligand.

```
NM_001134945
                                           (SEQ ID NO: 4)
atgtttactt gctggtggtc ttatctaaga tcaacattgg cagctgtgcc cggagaggcc tccagggtcc agagaaagga gtcgaagaag ccaccagcca agctgcagcc ccgagctcta gcaggctggc tccgcccgga agatggaggt caagcagaag gggcagagga tgaactggaa gtccggttca acgccccctt tgatgttgga atcaagctgt caggggttca gtaccagcag cacagccagg ccctggggaa gtttcttcag gacatcctct gggaagaggc caaagaggcc cagccgaca agtga NP_001128417
                                           (SEQ ID NO: 10)
mftcwwsylr stlaavpgea srvqrkeskk ppaklqpral agwlrpedgg qaegaedele vrfnapfdvq iklsqvqyqq hsqalgkflq dilweeakea padk
```

*Homo sapiens* ghrelin/obestatin prepropeptide (GHRL), transcript variant 5, mRNA and proteins (aa ----, and 25-47):
Transcript Variant: This variant (5) is generated from a more distal promoter, includes an alternate first exon which contains an upstream in-frame AUG codon, and omits two in-frame coding exons compared to variant 1. The resulting isoform (5) has a shorter and distinct N-terminus, as compared to isoform 1. Isoform 5 includes the obestatin ligand.

```
NM_001134946
                                           (SEQ ID NO: 5)
atgtttactt gctggtggtc ttatctaaga tcaacattgg cagctgtgcc cggagaggcc tccagggtcc agttcaacgc cccctttgat gttggaatca agctgtcagg ggttcagtac cagcagcaca gccaggccct ggggaagttt cttcaggaca tcctctggga agaggccaaa gaggcccag ccgacaagtg a NP_001128418
                                           (SEQ ID NO: 11)
mftcwwsylr stlaavpgea srvqfnapfd vqiklsqvqy qqhsqalgkf lqdilweeak eapadk
exon 3-deleted
```

Exon 3-Deleted Preproghrelin Variant [*Homo sapiens*]

```
AY184207
                                           (SEQ ID NO: 6)
atgccctccc cagggaccgt ctgcagcctc ctgctcctcg gcatgctctg gctggacttg gccatggcag gctccagctt cctgagccct gaacaccaga gagtccagca gagaaaggag tcgaagaagc caccagccaa gctgcagccc cgagctctag caggctggct ccgcccggaa gatggaggtc aagcagaagg ggcagaggat gaactggaag tccggaggcc cagccgaca agtgatcgcc cacaagcctt actcacctct ctctaa

AA027351
                                           (SEQ ID NO: 12)
```

```
-continued
mpspgtvcsl lllgmlwldl amagssflsp ehgrvggrke skkppaklgp ralagwlrpe dggqaegaed elevrrpqpt sdrpqallts l
```

REFERENCES CITED, AND INCORPORATED BY REFERENCE HEREIN FOR THEIR CITED RESPECTIVE TEACHINGS

1. M. Kojima et al., *Nature* 402, 656 (1999).
2. J. V. Zhang et al., *Science* 310, 996 (2005).
3. D. E. Cummings et al., *Diabetes* 50, 1714 (2001).
4. M. Tschöp et al., *J Endocrinol. Invest* 24, RC19 (2001).
5. M. A. Cowley et al., *Neuron* 37, 649 (2003).
6. B. Bodosi et al., *Am J Physiol Regul Integr Comp Physiol* 287, R1071 (2004).
7. S. Lu et al., *Neurosci. Lett.* 321, 157 (2002).
8. Y. Sun, S. Ahmed, R. G. Smith, *Mol. Cell. Biol.* 23, 7973 (2003).
9. D. E. Cummings, *Physiol Behav.* 89, 71 (2006).
10. G. J. Lagaud et al., *Biochem. Biophys. Res Commun.* 357, 264 (2007).
11. V. P. Carlini, H. B. Schioth, S. R. Debarioglio, *Biochem. Biophys. Res Commun.* 352, 907 (2007).
12. E. Bresciani et al., *J Endocrinol. Invest* 29, RC16 (2006).
13. De Smet B., T. Thijs, T. L. Peeters, I. Depoortere, *Neurogastroenterol. Motil.* 19, 211 (2007).
14. G. Gourcerol et al., *Peptides* 27, 2811 (2006).
15. É. Szentirmai, J. M. Krueger, *Neurosci. Lett.* 404, 222 (2006).
16. É. Szentirmai, I. Hajdu, F. Obal, Jr., J. M. Krueger, *Brain Res.* 1088, 131 (2006).
17. É. Szentirmai, L. Kapás, J. M. Krueger, *Am. J Physiol Regul. Integr. Comp Physiol* 292, R575 (2007).
18. É. Szentirmai, L. Kapás, Y. Sun, R. G. Smith, J. M. Krueger, *Am. J Physiol Regul. Integr. Comp Physiol* 293, R510 (2007).
19. Y. Sun, N. F. Butte, J. M. Garcia, R. G. Smith, *Endocrinology* 149, 843 (2007).
20. Y. Sun, P. Wang, H. Zheng, R. G. Smith, *Proc. Natl. Acad. Sci. U. S. A* 101, 4679 (2004).
21. G. Muccioli et al., *Eur. J Pharmacol* 498, 27 (2004).
22. K. Toshinai et al., *Endocrinology* 147, 2306 (2006).
23. C. Theander-Carrillo et al., *J Clin. Invest* 116, 1983 (2006).
24. T. Yasuda, T. Masaki, T. Kakuma, H. Yoshimatsu, *Neurosci. Lett.* 349, 75 (2003).
25. C. B. Lawrence, A. C. Snape, F. M. Baudoin, S. M. Luckman, *Endocrinology* 143, 155 (2002).
26. E. F. Gluck, N. Stephens, S. J. Swoap, *Am. J Physiol Regul. Integr. Comp Physiol* 291, R1303 (2006).
27. G. P. Webb, S. A. Jagot, M. E. Jakobson, *Comp Biochem. Physiol A* 72, 211 (1982).
28. J. Himms-Hagen, *Am. J Physiol* 248, E531 (1985).
29. O. Gavrilova et al., *Proc. Natl. Acad. Sci. U. S. A* 96, 14623 (1999).
30. F. Geiser, G. Körtner, I. Schmidt, *Am. J Physiol* 275, R1627 (1998).
31. I. Seim, C. C. Collet, A. C. Herington, L. K. Chopin, *BMC. Genomics* 8, 298 (2007).
32. De Smet B. et al., *J Pharmacol Exp. Ther.* 316, 431 (2006).
33. R. J. Berger, *Biol Psychol.* 19, 305 (1984).
34. S. J. Swoap, M. Rathvon, M. Gutilla, *Am. J Physiol Regul. Integr. Comp Physiol* 293, R468 (2007).
35. P. Alföldi, G. Rubicsek, G. Cserni, F. Obál, Jr., *Pflugers Arch.* 417, 336 (1990).
36. C. A. Czeisler, E. Weitzman, M. C. Moore-Ede, J. C. Zimmerman, R. S. Knauer, *Science* 210, 1264 (1980).
37. D. J. Dijk, C. A. Czeisler, *J. Neurosci.* 15, 3526 (1995).
38. P. L. Parmeggiani, C. Rabini, M. Cattalani, *Arch. Sci. Biol (Bologna.)* 53, 277 (1969).
39. W. R. Schmidek, K. Hoshino, M. Schmidek, C. Timo-Iaria, *Physiol Behav.* 8, 363 (1972).
40. B. Hale, D. Megirian, M. J. Pollard, *J Appl. Physiol* 57, 1564 (1984).
41. S. Sakaguchi, S. F. Glotzbach, H. C. Heller, *Am. J Physiol* 237, R80 (1979).
42. B. Roussel, P. Turrillot, K. Kitahama, *Brain Res* 294, 67 (1984).
43. M. Cerri et al., *Sleep* 28, 694 (2005).
44. P. Franken, I. Tobler, A. A. Borbely, *Physiol Behav.* 54, 885 (1993).
45. A. M. Strijkstra, S. Daan, *Am. J Physiol* 275, R1110 (1998).
46. J. R. Pappenheimer, G. Koski, V. Fencl, M. L. Karnovsky, J. Krueger, *J. Neurophysiol.* 38, 1299 (1975).
47. J. E. Larkin, C. H. Heller, *Sleep Res Online* 1, 96 (1998).

The invention claimed is:

1. A method for suppressing food intake or appetite, comprising:
   administration to a mammalian subject in need thereof an amount of ghrelin or preproghrelin siRNA agent sufficient to suppress ghrelin or preproghrelin mRNA, wherein the ghrelin or preproghrelin siRNA agent, comprises a nucleic acid sequence of at least 19 contiguous nucleotides identical or complementary to the preproghrelin mRNA sequence encoding the first 5 amino acids (Phe-Asn-Ala-Pro-Phe) (SEQ ID NO:18) of obestatin, and wherein suppression of food intake or appetite is afforded.

2. A method for reducing body weight or treating obesity, comprising:
   administration to a mammalian subject in need thereof an amount of ghrelin or preproghrelin siRNA agent sufficient to suppress ghrelin or preproghrelin mRNA, wherein, the ghrelin or preproghrelin siRNA agent comprises a nucleic acid sequence of at least 19 contiguous nucleotides identical or complementary to the preproghrelin mRNA sequence encoding the first 5 amino acids (Phe-Asn-Ala-Pro-Phe)(SEQ ID NO: 18) of obestatin, and wherein reduction of body weight or treating obesity is afforded.

3. The method of any one of claims 1 through 2, wherein the ghrelin or preproghrelin siRNA agent, comprises a sequence complementary to a target sequence selected from SEQ ID NOS:1-5, complements thereof, and contiguous portions thereof.

4. The method of claim 3, wherein the siRNA agent comprises overhanging ends, which may or may not be complementary to the target sequence.

5. The method of any one of claims 1 through 2, wherein administration comprises oral delivery.

6. The method of claims 1 through 2, wherein the suppression of ghrelin or preproghrelin mRNA is transient or reversible.

7. A method for reducing body temperature or induction of hypothermia, comprising:
   administration to a mammalian subject in need thereof an amount of obestatin siRNA agent sufficient to suppress obestatin mRNA, wherein the obestatin siRNA agent, comprises a nucleic acid sequence of at least 19 contiguous nucleotides identical or complementary to the preproghrelin mRNA sequence encoding the first 5 amino acids (Phe-Asn-Ala-Pro-Phe) (SEQ ID NO:18) of obestatin, and wherein reducing body temperature or induction of hypothermia is afforded.

8. The method of claim 7, wherein the obestatin siRNA agent, comprises a sequence complementary to a target sequence selected from SEQ ID NOS:1-5, complements thereof, and contiguous portions thereof.

9. The method of claim 8, wherein the siRNA agent comprises overhanging ends, which may or may not be complementary to the target sequence.

10. The method of claim 7, wherein administration comprises oral delivery.

11. The method of claim 7, wherein suppression of obestatin mRNA is transient or reversible.

12. The method of claim 7, wherein reducing body temperature or induction of hypothermia comprises regulating at least one of surgical hypothermia, trauma-related hypothermia, and cardiac-related hypothermia.

* * * * *